(12) United States Patent
Maruo et al.

(10) Patent No.: US 8,702,950 B2
(45) Date of Patent: Apr. 22, 2014

(54) DEVICE FOR ELECTROPHORESIS, DEVICE FOR TRANSFER, DEVICE FOR ELECTROPHORESIS AND TRANSFER, CHIP FOR ELECTROPHORESIS AND TRANSFER, AND METHOD FOR ELECTROPHORESIS, METHOD FOR TRANSFER, AND METHOD FOR ELECTROPHORESIS AND TRANSFER

(75) Inventors: Yuji Maruo, Nagareyama (JP); Yutaka Unuma, Matsudo (JP); Atsunori Hiratsuka, Tokyo (JP); Hideki Kinoshita, Tokyo (JP); Kenji Yokoyama, Tsukuba (JP); Koji Sakairi, Tokyo (JP); Satonari Akutsu, Tokyo (JP)

(73) Assignees: Sharp Kabushiki Kaisha, Osaka (JP); Toppan Printing Co., Ltd., Tokyo (JP)

( * ) Notice: Subject to any disclaimer, the term of this patent is extended or adjusted under 35 U.S.C. 154(b) by 0 days.

(21) Appl. No.: 13/607,844

(22) Filed: Sep. 10, 2012

(65) Prior Publication Data

US 2013/0015069 A1    Jan. 17, 2013

Related U.S. Application Data

(62) Division of application No. 12/130,691, filed on May 30, 2008, now abandoned.

(30) Foreign Application Priority Data

| May 31, 2007 | (JP) | 2007-146215 |
|---|---|---|
| May 31, 2007 | (JP) | 2007-146235 |
| May 31, 2007 | (JP) | 2007-146276 |

(51) Int. Cl.
*G01N 27/26*    (2006.01)
*B01D 57/02*    (2006.01)

(52) U.S. Cl.
USPC ........... 204/614; 204/627; 204/629; 204/641; 204/610; 204/548; 204/464; 204/450; 204/600; 422/68.1; 422/82.01; 435/287.1

(58) Field of Classification Search
USPC ......... 204/547, 643, 450, 600, 459, 610, 548, 204/464, 614, 627–629, 641; 422/68.1, 422/82.01; 435/287.1
See application file for complete search history.

(56) References Cited

U.S. PATENT DOCUMENTS

| 4,726,889 A | 2/1988 | Love et al. |
|---|---|---|
| 4,756,809 A | 7/1988 | Love et al. |

(Continued)

FOREIGN PATENT DOCUMENTS

| JP | 62-185157 A | 8/1987 |
|---|---|---|
| JP | 64-80851 A | 3/1989 |

(Continued)

OTHER PUBLICATIONS

Office Action mailed Sep. 21, 2011 in U.S. Appl. No. 12/130,691 (7 pages).

(Continued)

*Primary Examiner* — Jennifer Dieterle
(74) *Attorney, Agent, or Firm* — Nixon & Vanderhye P.C.

(57) ABSTRACT

A device for electrophoresis applies a voltage to a medium in contact with a plurality of electric conductors so that a potential of adjacent conductors is within a certain range. This allows preventing decline in electrophoresis speed. A device for electrophoresis and transfer includes an electrode having a plurality of electrode regions being insulated one another and arranged in a specific direction. This allows providing a practical and easy-to-use device for electrophoresis and transfer. A device for transfer alters an applied voltage or applied voltage duration to a certain position to another position. This allows improving transfer efficiency.

16 Claims, 27 Drawing Sheets

(56) References Cited

U.S. PATENT DOCUMENTS

| | | | | |
|---|---|---|---|---|
| 4,849,078 | A | 7/1989 | Love et al. | |
| 4,889,606 | A | 12/1989 | Dyson et al. | |
| 4,911,816 | A | 3/1990 | Love et al. | |
| 4,994,166 | A * | 2/1991 | Fernwood et al. | 204/614 |
| 5,126,022 | A | 6/1992 | Soane et al. | |
| 5,234,559 | A * | 8/1993 | Collier et al. | 204/464 |
| 5,445,723 | A * | 8/1995 | Camacho | 204/614 |
| 5,750,015 | A | 5/1998 | Soane et al. | |
| 5,770,029 | A | 6/1998 | Nelson et al. | |
| 5,773,645 | A | 6/1998 | Hochstrasser | |
| 5,840,169 | A | 11/1998 | Andersen | |
| 5,858,188 | A | 1/1999 | Soane et al. | |
| 5,935,401 | A | 8/1999 | Anigo | |
| 6,007,690 | A | 12/1999 | Nelson et al. | |
| 6,054,034 | A | 4/2000 | Soane et al. | |
| 6,056,860 | A | 5/2000 | Amigo et al. | |
| 6,074,827 | A | 6/2000 | Nelson et al. | |
| 6,093,296 | A | 7/2000 | Soane et al. | |
| 6,176,962 | B1 | 1/2001 | Soane et al. | |
| 6,296,752 | B1 * | 10/2001 | McBride et al. | 204/547 |
| 6,306,272 | B1 | 10/2001 | Soane et al. | |
| 6,344,326 | B1 | 2/2002 | Nelson et al. | |
| 6,413,400 | B1 | 7/2002 | Soane et al. | |
| 6,808,609 | B1 | 10/2004 | Soane et al. | |
| 6,969,615 | B2 | 11/2005 | Knezevic et al. | |
| 8,419,916 | B2 | 4/2013 | Sakairi et al. | |
| 2002/0053399 | A1 | 5/2002 | Soane et al. | |
| 2002/0056640 | A1 | 5/2002 | Soane et al. | |
| 2002/0119482 | A1 | 8/2002 | Nelson et al. | |
| 2002/0160536 | A1 * | 10/2002 | Regnier et al. | 436/518 |
| 2003/0032201 | A1 | 2/2003 | Flesher | |
| 2003/0215937 | A1 * | 11/2003 | Matson | 435/287.2 |
| 2003/0224436 | A1 | 12/2003 | Nelson et al. | |
| 2004/0121488 | A1 | 6/2004 | Chang et al. | |
| 2004/0251139 | A1 | 12/2004 | Lean et al. | |
| 2004/0262159 | A1 | 12/2004 | Martin et al. | |
| 2006/0042951 | A1 * | 3/2006 | Ohse et al. | 204/600 |
| 2007/0045118 | A1 | 3/2007 | Maruo et al. | |
| 2007/0278102 | A1 | 12/2007 | Hayashida et al. | |
| 2008/0296158 | A1 | 12/2008 | Maruo et al. | |
| 2010/0044228 | A1 | 2/2010 | Baumann et al. | |
| 2011/0233062 | A1 | 9/2011 | Sakairi et al. | |

FOREIGN PATENT DOCUMENTS

| | | |
|---|---|---|
| JP | 2-1544 | 1/1990 |
| JP | 4-42050 A | 2/1992 |
| JP | 5-4003 U | 1/1993 |
| JP | 5-4004 U | 1/1993 |
| JP | 5-504628 A | 7/1993 |
| JP | 7-506421 A | 7/1995 |
| JP | 9-89840 A | 4/1997 |
| JP | 2000-28578 A | 1/2000 |
| JP | 2005-3864 A | 1/2005 |
| JP | 2006-71494 A | 3/2006 |
| JP | 2007-64848 A | 3/2007 |
| JP | 2007-71609 A | 3/2007 |
| WO | 91/12904 A1 | 9/1991 |
| WO | 93/16788 A1 | 9/1993 |
| WO | 97/38300 A1 | 10/1997 |
| WO | 98/04909 A1 | 2/1998 |
| WO | 98/12530 A2 | 3/1998 |
| WO | 98/45693 A1 | 10/1998 |
| WO | 99/40174 A1 | 8/1999 |
| WO | WO 2004046711 * | 6/2004 |
| WO | WO2007/029666 | 3/2007 |
| WO | WO2007/125790 | 11/2007 |
| WO | WO2007/138482 | 12/2007 |

OTHER PUBLICATIONS

Office Action mailed Dec. 5, 2011 in U.S. Appl. No. 12/130,691 (14 pages).

Office Action mailed May 10, 2012 in U.S. Appl. No. 12/130,691 (22 pages).

Advisory Action mailed Jul. 18, 2012 in U.S. Appl. No. 12/130,691 (3 pages).

Ofuji, "Denkieidou Naruhodo Q&A", (Electrophoreses Q&A), Yodosha in 2005, pp. 161-163 (with partial English translation).

Gershoni et al, "Protein Blotting in Uniform or Gradient Electric Fields", Analytical Biochemistry, vol. 144, Issue 1, 1985, pp. 32-40.

Svoboda et al, "Rapid Electrotransfer of Proteins from Polyacrylamide Gel to Nitrocellulose Membrane Using Surface-Conductive Glass as Anode", Analytical Biochemistry, vol. 151, Issue 1, 1985, pp. 16-23.

Himber, "Horizontal Semi-Dry Electroblotting for the Detection of the Low Density Lipoprotein Receptor in Solubilized Liver Membranes", Electrophoresis, vol. 14, No. 8, 1993, pp. 794-797.

Notification of Reason for Refusal mailed Mar. 6, 2012 in Japanese Application No. 2008-266759, with English translation (5 pages).

Notice of Allowance mailed Dec. 24, 2012 in U.S. Appl. No. 13/073,835.

* cited by examiner

FLUORESCENT M.W.   VISIBLE M.W.
1    #2            #3    #4

FLUORESCENT M.W.   VISIBLE M.W.
1    #2            #3    #4

| MOLECULAR WEIGHT (k) | 10V | 20V | 30V | 40V |
|---|---|---|---|---|
| 200 | 9977 (9.69) | 11430 (13.68) | 11417 (9.02) | 10652 (7.58) |
| 116 | 14686 (9.41) | 15932 (7.75) | 17028 (8.46) | 14535 (13.94) |
| 97 | 7745 (18.82) | 10888 (18.67) | 15889 (13.13) | 11382 (15.04) |
| 66 | 25979 (13.63) | 30275 (3.25) | 32674 (7.96) | 25016 (7.68) |
| 42 | 17376 (8.92) | 14115 (4.29) | 15670 (20.15) | 11319 (10.59) |
| 36 | 36370 (1.15) | 34317 (5.44) | 36063 (10.43) | 28927 (15.37) |
| 28 | 10163 (25.59) | 10084 (27.90) | 9052 (20.09) | 5986 (30.31) |

DEVICE FOR ELECTROPHORESIS, DEVICE FOR TRANSFER, DEVICE FOR ELECTROPHORESIS AND TRANSFER, CHIP FOR ELECTROPHORESIS AND TRANSFER, AND METHOD FOR ELECTROPHORESIS, METHOD FOR TRANSFER, AND METHOD FOR ELECTROPHORESIS AND TRANSFER

CROSS-REFERENCES TO RELATED APPLICATIONS

This application is a divisional of U.S. patent application Ser. No. 12/130,691, filed May 30, 2008, now abandoned and incorporated herein by reference; which Nonprovisional application claims priority under 35 U.S.C. §119(a) on Patent Applications No. 146215/2007, No. 146235/2007, and No. 146276/2007 each filed in Japan on May 31, 2007, the entire contents of which are hereby incorporated by reference.

TECHNICAL FIELD

The technology presented herein relates to devices for electrophoresis, transfer, and electrophoresis and transfer, and methods for electrophoresis, transfer, and electrophoresis and transfer.

BACKGROUND AND SUMMARY

In the life science field, electrophoresis is one of the significantly useful separating and analyzing techniques. It is used for separating biopolymers, such as protein, DNA, RNA, and the like. It is also possible to separate cells. In addition to a typical electrophoresis method with use of gel, a Capillary electrophoresis method with use of buffer solutions containing a polymer and a Free Flow Electrophoresis method carried out in free solution have been performed.

As a technique to improve electrophoresis, Japanese Utility Model Publication, Jitsukaihei, No. 5-4004 (date of publication: Jan. 22, 1999) discloses that disruption in electrophoresis pattern due to uneven electrophoresis field is prevented by providing a wire-shaped electric conductor in an electrophoresis chamber.

Also, Japanese Utility Model Publication, Jitsukaihei, No. 5-4003 (date of publication: Jan. 22, 1993) discloses that provision of an intermediate electrode in an electrophoresis chamber actively controls distributions of electric fields and electric potentials in the electrophoresis chamber.

As a result of study, however, the present inventors identified that the electrophoresis devices having an electric conductor in an electrophoresis chamber, such as the electrophoresis devices in the above documents have a problem of decline in electrophoresis speed.

Also, in Proteome analysis, it is necessary to simplify a series of procedures including first electrophoresis, second electrophoresis, and transferring a sample to a membrane, which are carried out continuously.

Japanese Publication for Unexamined Patent Application, Tokukai, No. 2007-64848 (date of publication: Mar. 15, 2007) discloses an electrophoresis device for automating the first electrophoresis and the second electrophoresis.

Japanese Publication for Unexamined Patent Application, Tokukai, No. 2000-28578 (date of publication: Jan. 28, 2000) discloses a device for electrophoresis and transfer.

However, a device disclosed in Japanese Publication for Unexamined Patent Application, Tokukai, No. 2000-28578 (date of publication: Jan. 28, 2000) still requires a complicated and skillful procedure such as a removal of gel after an electrophoresis.

Japanese Publication for Unexamined Patent Application, Tokukai, No. 2006-71494 (date of publication: Mar. 16, 2006) proposes an easy-operation device for electrophoresis and transfer which does not require the removal of gel.

However, a practical and easy-operation device for electrophoresis and transfer is not yet in existence.

According to the study of the present inventors, electrophoresis devices merely having an electrode for transfer in the middle of the electrophoresis path, such as a device disclosed in Japanese Publication for Unexamined Patent Application, Tokukai, No. 2006-71494 (date of publication: Mar. 16, 2006), have a difficulty in performing an electrophoresis. Specifically, the electrophoresis device with the above structure failed to apply a voltage and migrate a sample in the process of electrophoresis.

Further, in analyzing a result of an electrophoresis, it is widely performed that a sample in gel are transferred to a membrane and carrying out an antigen antibody reaction on the membrane.

As a method for transferring a sample in gel to a membrane, there are several methods such as a way of using capillary action and a way of using a voltage difference. (Referring to a book "DENKIEIDOU NARUHODO Q&A" ("Electrophoresis Q & A") P. 161 to 163, written by Michihiro Ofuji, published by Yodosha in 2005)

However, the present inventors identified that transfer efficiency was declined in some samples in transferring them in gel to a membrane under a conventional transfer method.

A first feature of an example embodiment presented herein is to prevent decline in electrophoresis speed in an electrophoresis device including an electric conductor in an electrophoresis chamber.

As a result of diligent studies, the present inventors identified that a cause of the decline in electrophoresis speed was in a conventionally unidentified phenomenon. The phenomenon is that air bubbles generated at an electric conductor in an electrophoresis chamber detach gel from the electric conductor, and a buffer solution goes into the gap between the gel and the electric conductor, thereby attaining inhibition of a buffer action.

Then, the present inventors studied further and found that the air bubbles are not generated when an electric potential difference between adjacent electric conductors is under a certain voltage, and accomplished the invention based on the finding.

Namely, a device for electrophoresis of the present embodiment is configured to separate separation target components in a medium in which a plurality of electric conductors are provided in contact with the medium, including voltage applying means configured to apply a voltage to the medium, so that a potential difference between adjacent electric conductors is more than 0V but not more than 0.3V.

With this structure, the voltage applying means applies a voltage so that a potential difference between adjacent electric conductors is more than 0V but not more than 0.3V. If the potential difference between adjacent electric conductors is not more than 0.3, no air bubbles generate as shown in embodiment examples described later. Therefore, this structure is capable of suppressing decline in electrophoresis speed due to the emergence of air bubbles.

In the electrophoresis device with this structure, the voltage applying means may apply the voltage to each of the electric conductors.

According to this structure, the voltage applying means may apply a potential to each of the electric conductors directly so that it is easy to set a potential difference between adjacent electric conductors more than 0V but not more than 0.3V.

It is preferable that the device for electrophoresis has 250 or more electric conductors.

According to this structure, it is easy to control a potential difference between adjacent electric conductors not more than 0.3V by only applying a voltage which is in normal range voltage for electrophoresis (from 50V to 500V) to gel.

It is preferable that the electric conductor is line-shaped in the device for electrophoresis.

With this structure, it is easy to control a potential difference between adjacent electric conductors not more than 0.3V with use of narrow line-shaped electric conductors which allow arranging a number of electric conductors.

It is preferable that the line-shaped electric conductors are arranged in parallel one another and extend in an orthogonal direction to the direction in which the voltage applying means applies a voltage to the medium.

According to this structure, the line-shaped electric conductors are arranged in parallel one another and extend in an orthogonal direction to the direction in which the voltage applying means applies a voltage to the medium. Therefore, the electric conductors do not affect a potential gradient toward the first direction, thereby making it possible to separate the separation target components in the medium favorably.

It is preferable that the line-shaped electric conductor is not more than 10 μm in thickness in the device for electrophoresis.

With this structure, it is easy to control a potential difference between adjacent electric conductors not more than 0.3V with use of the narrow line-shaped electric conductors which allow arranging a number of electric conductors even in a small sized device.

It is preferable that the distance between adjacent electric conductors is not more than 100 μm in the device for electrophoresis.

With this structure, it is easy to control a potential difference between adjacent electric conductors not more than 0.3V because of the narrow space between the electric conductors, which allows arranging a number of electric conductors even in a small sized device.

It is preferable in the device for electrophoresis that the electric conductor is made of metal selected from the group consisting of platinum, zinc, and copper.

This structure allows performing a method for electrophoresis of the present embodiment repeatedly because the electric conductor is less likely to be deteriorated.

The device for electrophoresis may be an isoelectric electrophoresis device.

This structure allows forming a uniform pH gradient in a medium in an isoelectric electrophoresis device.

A method for the electrophoresis of the present embodiment is a method for separating separation target components in a medium in which a plurality of electric conductors are provided in contact with the medium, including applying a voltage to the medium so that a potential difference between adjacent electric conductors is more than 0V but not more than 0.3V.

With this arrangement, in the process of applying voltage, a voltage is applied so that a potential difference between adjacent electric conductors is more than 0V but not more than 0.3V. When the voltage between the adjacent electric conductors is not more than 0.3V, air bubbles do not generate. Therefore, this arrangement allows preventing the decline in electrophoresis speed due to the generation of air bubbles.

A second feature of the present embodiment is to provide a practical and easy-to-use device for electrophoresis and transfer, a chip for electrophoresis and transfer, and a method for electrophoresis and transfer.

As a result of diligent studies, the present inventors found that it is possible to perform an electrophoresis with ease, even though an electrode for transfer is provided in the middle of the electrophoresis path, by using the electrode having a plurality of electrode regions being insulated one another and arranged in a direction of electrophoresis path.

Namely, a device for electrophoresis and transfer of the present embodiment includes first voltage applying means configured to apply a voltage with respect to a specific direction in the first medium having separation target components, and second voltage applying means configured to apply a voltage to the first medium toward a direction of a second medium being in contact with the first medium, the second voltage applying means including a first electrode having a plurality of electrode regions being insulted one another and arranged in the specific direction.

According to this structure, the device for electrophoresis and transfer of the present embodiment can separate separation target components in the first medium, and then transfer the separated separation target components to the second medium. For example, it is very useful to use the device for electrophoresis and transfer which can perform both an electrophoresis and a blotting easily in an analysis of biopolymer.

In a conventional device for electrophoresis and transfer, however, the electrode, which is provided in the second voltage applying means for transferring separation target components in a first medium to a second medium, hampers the separation of the separation target components in the first medium. Therefore, the conventional device was not useful.

However, with this structure, the second voltage applying means includes the first electrode having a plurality of electrode regions being insulated one another and arranged in the specific direction. Since the electrode regions in the first electrode are insulated one another and arranged in the specific direction, the separation of the separation target components in the first medium is not hampered. Namely, with this structure, it is possible to perform an electrophoresis and a transfer practically and easily.

It is preferable that the electrode region is line-shaped in the device for electrophoresis and transfer.

According to this structure, each of the electrode regions is line-shaped which enables to fill up the surface easily when they are arranged in the specific direction. This allows transferring the separation target components in the first medium to the second medium efficiently.

It is preferable that the plurality of electrode regions are arranged in parallel one another and extend in an orthogonal direction to the specific direction in the device for electrophoresis and transfer.

The line-shaped electrode regions arranged in parallel one another and extending in an orthogonal direction to the specific direction do not affect the voltage applied to the specific direction. This allows separating separation target components in the first medium favorably.

It is more preferable that the device for electrophoresis and transfer further includes wire connection means configured to switch the first electrode between connection and disconnection.

With this structure, it is possible to control a potential of the first electrode easily because the wire connection means is capable of switching the first electrode between connection and disconnection.

The second voltage applying means may further include a detachable second electrode in the device for electrophoresis and transfer.

According to this structure, the second voltage applying means has a detachable second electrode as well as the first electrode. This allows transferring the separation target components in the first medium to the second medium with ease without affecting the separation of separation target components in the first medium.

The device for electrophoresis and transfer may include a detachable holder configured to hold the second electrode and the second medium.

According to this structure, the second medium is easy to be used for further analysis since the second medium is detachable.

The second voltage applying means may further include a second electrode having a plurality of electrode regions being insulated one another and arranged in the specific direction in the device for electrophoresis and transfer.

According to this structure, the electrode regions in the second electrode do not hamper the separation of the separation target components in the first medium because the electrode regions are insulated one another and are arranged in the specific direction in which the separation target components in the first medium are separated. Therefore, it is possible to transfer the separation target components in the first medium to the second medium with ease without affecting the separation of separation target components in the first medium.

A chip for electrophoresis and transfer of the present embodiment includes a separation section configured to place a first medium having separation target components, and a second medium in contact with the first medium, a first buffer solution chamber and a second buffer solution chamber sandwiching the separation section, and a first electrode being provided on the separation section, and having a plurality of electrode regions being insulated one another and arranged in the specific direction specified by the first and the second buffer solution chambers.

According to this structure, it is possible to separate the separation target components in the first medium toward the specific direction by applying a voltage to the first medium provided on the separation section via the electrodes arranged in the first and second buffer solution chambers. At this time, the first electrode, which is provided on the separation section, has the electric regions being insulated one another and arranged in the above direction. This allows not affecting to the separation of the separation target components in the first medium.

The device realizes both electrophoresis and transfer because the first electrode allows applying a voltage to the separated separation target components easily, in a direction from the first medium toward the second medium.

A method for electrophoresis and transfer of the present embodiment includes (a) applying a voltage to the first medium having separation target components in the specific direction, and (b) applying a voltage to the first medium toward a direction of the second medium being in contact with the first medium, following the step (a), wherein in the step (b), the voltage is applied with use of the first electrode including a plurality of electrode regions being insulated one another and arranged in the specific direction.

With this arrangement, it is possible to perform electrophoresis and transfer favorably because the first electrode which is used in the second voltage applying process do not adversely affect the separation of the separation target components in the first medium in the first voltage applying process.

A third object of the present embodiment is made in view of the foregoing problem and is for providing a device for transfer preventing decline in transfer efficiency.

As a result of diligent sturdy, the inventors of the present embodiment found that there is a suitable transfer voltage depending on a molecular weight of a sample to be transferred and also found that it is possible to prevent decline in transfer efficiency by adjusting an applied voltage to the medium including the sample depending on positions. The present embodiment is accomplished based on the finding.

Namely, a device for transfer of the present embodiment is configured to transfer target components in the first medium to the second medium, including voltage applying means configured to apply a voltage to the first medium, the voltage applying means applying the voltage to the first medium in such a manner that a certain position and another position in the first medium are provided different voltages or different voltage durations.

With this structure, the transfer target components in the first medium such as agarose gel are transferred to the second medium such as a membrane by applying a voltage to the first medium. The voltage applied to the first medium varies depending on positions in the first medium. This allows applying a suitable voltage depending on a molecular weight of each of the transfer target components in the first medium, for example, SDS-PAGE separated polyacrylamide gel including transfer target components whose molecular weights differ in position in the gel.

According to the findings of the present inventors, there is a suitable voltage for transfer depending on a molecular weight of a transfer target component. In other words, the transfer efficiency declines when a voltage far from the suitable voltage is applied to the transfer target component. This structure allows applying a suitable voltage depending on the molecular weight of each of the transfer target components and preventing decline in transfer efficiency.

As described later, it is possible to obtain the same effect by adjusting a voltage duration applied to the transfer target components instead of adjusting an applied voltage to the transfer target components.

It is preferable that the voltage applying means increases the voltage stepwise or gradually toward the specific direction specified by the first medium in the device for transfer.

According to this structure, the voltage applied to the first medium increases toward the specific direction specified by the first medium. Accordingly, it is possible to apply a suitable voltage depending on the molecular weight of each of the transfer target components in the first medium such as polyacrylamide gel separated by SDS-PAGE including transfer target components in which the distribution of the molecular weight increases in one way.

The voltage applying means may increase an applied voltage duration stepwise or gradually toward the specific direction specified by the first medium in the device for transfer.

As described above, it is possible to obtain the same effect by adjusting a voltage duration applied to transfer target components instead of adjusting an applied voltage to transfer target components.

It is preferable that the voltage applying means includes the first electrode and the second electrode, each of which is divided into a plurality of electrode regions being insulated one another in the device for transfer.

According to this structure, each of the first and the second electrodes includes a plurality of electrode regions being insulated one another. Therefore, it is possible to provide a different potential to each of the electrode regions or a different potential duration to each of the electrode regions with ease.

It is preferable that the voltage applying means includes the first electrode and the second electrode, each of which is divided into a plurality of electrode regions arranged in the specific direction in the device for transfer.

According to this structure, each of the first and the second electrodes is divided into a plurality of electrode regions being insulated one another and arranged in the specific direction. Therefore, it is possible to increase an applied voltage or a voltage duration applied to the first medium toward the specific direction with ease.

It is preferable that each divisional shape of the electrode regions of the first electrode and each divisional shape of the electrode regions of the second electrode are substantially equal in the device for transfer.

According to this structure, it is possible to apply a voltage to the first medium accurately because the divisional shape of the electrode regions of the first electrode and the second electrode are substantially equal. Namely, an electrode region of the first electrode and a corresponding electrode region of the second electrode have a substantially equal shape. Therefore, an electric field applied by a potential difference between the first and the second electrode regions is easily predictable because the electric field is based on the shape of both electrode regions.

It is preferable that the electrode region is line-shaped in the device for transfer.

According to this structure, it is possible to generate a fine potential difference because each of the electrode regions is line-shaped.

It is preferable that the line-shaped electrode regions are arranged in parallel one another and extend in an orthogonal direction to the specific direction in the device for transfer.

This structure allows dividing a potential finely toward the specific direction.

The voltage applying means may apply the voltage to each of the electrode regions in the device for transfer.

This structure allows the voltage applying means to apply a potential to the electrode regions directly. Therefore, it is possible to adjust an applied voltage in accordance with the molecular weight of the transfer target components with ease.

In the device for transfer, the voltage applying means includes at least one power supply, and a plurality of conductive paths connecting the power supply and each of the electrode regions conductively, and the conductive paths may have at least two kinds of resistance values.

According to this structure, the conductive paths conductively connecting the power supply and each of the electrode regions have two or more kinds of resistance values. This allows applying two or more kinds of potentials to each of the electrode regions depending on the molecular weight of the transfer target components.

In the device for transfer, the voltage applying means may alter a potential duration applied to each of the electrode regions.

According to this structure, it is possible to apply a voltage for a suitable time period to the transfer target components depending on a molecular weight of each component because the voltage applying means controls a potential duration applied to the electrode regions.

In the device for transfer, the voltage applying means includes a power supply and a mobile electric conductive section conductively connecting the power supply and the plurality of conductive regions, and the mobile electric conductive section may alter duration of potential application to each of the electrode regions by its movement.

This structure allows the voltage applying means to control a potential duration applied to each of the electrode regions with ease.

The mobile electric conductive section may be bar-shaped in the device for transfer.

This structure allows the potential control means to control a potential duration applied to each of the electrode regions with ease.

In the device for transfer of the present embodiment, the voltage applying means applies the voltage to the first medium via an electric resistance layer, and a certain position and another position on the electric resistance layer may have different resistance values.

According to this structure, the voltage applying means applies a voltage to the first medium via the electric resistance layer and the electric resistance layer have various resistance values depending on positions. This allows the voltage applying means to apply different voltages to the first medium by positions with ease.

It is preferable that the voltage applying means applies a voltage to the first medium via the electric resistance layer in which a resistance value decreases stepwise or gradually to the specific direction specified by the first medium.

According to this structure, since the electric resistance layer has a stepwise or gradually decreasing resistance value to the specific direction specified by the first medium, the voltage applying means is able to increase an applied voltage stepwise or gradually to the first medium to the specific direction with ease.

It is preferable that the device for transfer further includes cooling means for cooling the voltage applying means.

According to this structure, the cooling means radiates heat in the voltage applying means and maintains optimum temperatures for the first and the second mediums, thereby making it possible to prevent affecting both mediums and the transfer target components qualitatively.

A method for transfer of the present embodiment is a method for transferring transfer target components in a first medium to a second medium including applying a voltage to the first medium, in such a manner that a certain position and another position in the first medium are provided different voltages or different potential durations.

According to this structure, it is possible to prevent decline in transfer efficiency by applying a suitable voltage depending on a molecular weight of each of the transfer target components same as the device for transfer of the present embodiment.

Additional features, and strengths of the present embodiment will be made clear by the description below. Further, the advantages of the present embodiment will be evident from the following explanation with reference to the drawings.

DESCRIPTION OF THE EMBODIMENTS

[1: Device for Electrophoresis and Method for Electrophoresis]

Figure 1:
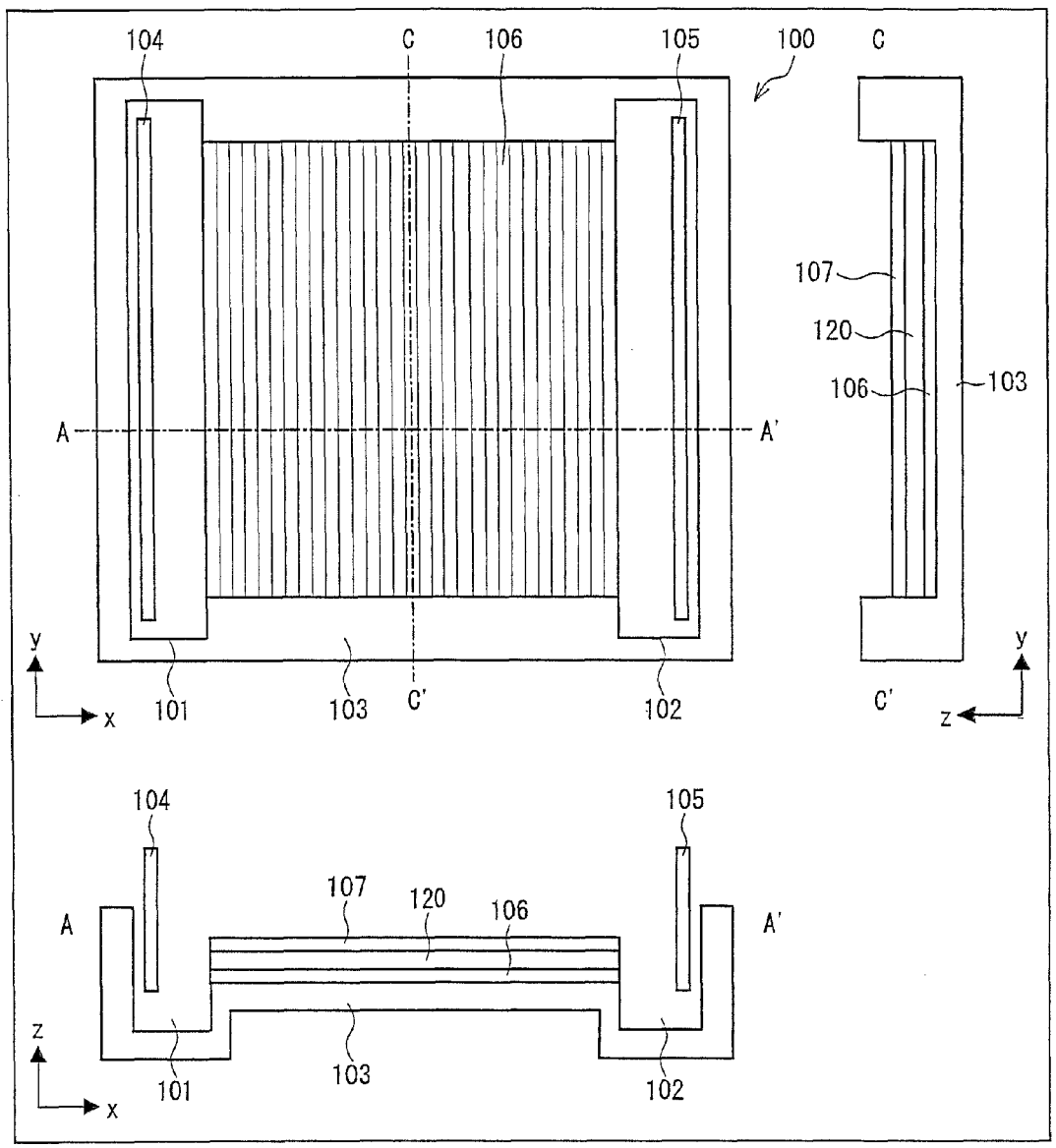
FIG. 1 is a schematic view illustrating a structure of a device for electrophoresis according to an embodiment.

The following explanation deals with an embodiment of a device for electrophoresis according to FIG. 1.

The device for electrophoresis 100 of the present embodiment includes buffer solution chambers 101 and 102, a separation section 103, electrodes 104 and 105 (voltage applying means), a stripe electrode 106 (electric conductors), and a lid member 107. The buffer solution chambers 101 and 102 are filled with a buffer solution and provided with the electrodes 104 and 105 therein, respectively. The separation section 103 is sandwiched between the buffer solution chambers 101 and 102. The stripe electrode 106 is provided on the separation section 103, and a medium 120 is provided on the stripe electrode 106 in the separation section 103.

As the buffer solution, a buffer solution which has a composition generally used for electrophoresis is applicable. Also, the medium 120 is made from a gel generally used for electrophoresis such as an agarose gel, a polyacrylamide, and the like and contains separation target components. The separation target components are the components to be separated and analyzed by electrophoresis and transfer. The separation target components may be prepared preferably from biological materials such as bions, biological fluid, cell strains, cultured tissues, and fragment tissues.

The electrodes 104 and 105 apply a voltage to the medium 120 so that a potential difference between stripe electric conductors 106 is not more than 0.3 V. This makes it possible to prevent the generation of air bubbles. The voltage applied by the electrodes 104 and 105 is calculated by the number of electric conductors in the stripe electrode 106 and the following formula (I) is satisfied. Note that the applied voltage should exceed 0V.

$$\text{Applied voltage(V)(the number of electric conductors}-1)\times 0.3 \text{ (V)} \tag{1}$$

As one aspect, the device for electrophoresis 100 of the present embodiment may have potential control means (voltage applying means), which is not illustrated in the drawings, for controlling a potential of each electric conductor in a stripe electric conductor 113. The potential control means, for example, includes a power supply, and conductive paths. The power supply is conductively connected to each of the electric conductors via a sub power supply or conductive paths, each of which has a different resistance value. This allows the potential control means to apply a different voltage to each of the electric conductors. Note that it is not necessary to control potentials of all the electric conductors. Potentials of some electric conductors (called intermediate electrodes hereinafter) may be controlled. In this case, the other electric conductors sandwiched between the intermediate electrodes have a potential based on a potential gradient created by each of the intermediate electrodes. In any cases, the potential should be applied so that the potential difference of the adjacent electric conductors is not more than 0.3 V. This allows preventing the generation of air babbles.

In addition to the above effect, the potential control means contributes to favorably carrying out the electrophoresis. For example, the electrophoresis may be carried out with a greater potential gradient in a low potential range and a smaller potential gradient in a high potential range. The greater potential gradient in the low potential range allows greater separation of high polymer weight components which are difficult to separate, among the separation target components in the medium 120, while the smaller potential gradient in the high potential range retains in the medium 120 such fast-migrating low polymer weight components among the separation target components in the medium 120. This allows favorable separation of the separation target components, which include wide range of molecular weight components. Namely, in electrophoresis, components migrate from a low potential side to a high potential side. High polymer weight components remain on the low potential side and low polymer weight components tend to migrate to the high potential side. As described above, it is possible to increase the degree of separation of high polymer weight components by increasing the potential gradient of a low potential range and hamper the migration of low polymer weight components by decreasing the potential gradient of a high potential range.

Figure 2:
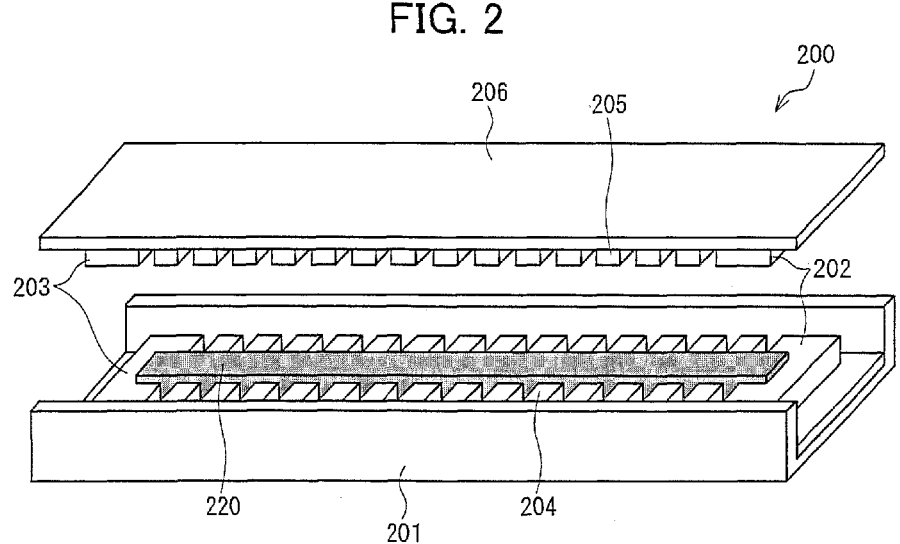
FIG. 2 is a perspective view illustrating a structure of an isoelectric electrophoresis device according to another embodiment.
Figure 3:
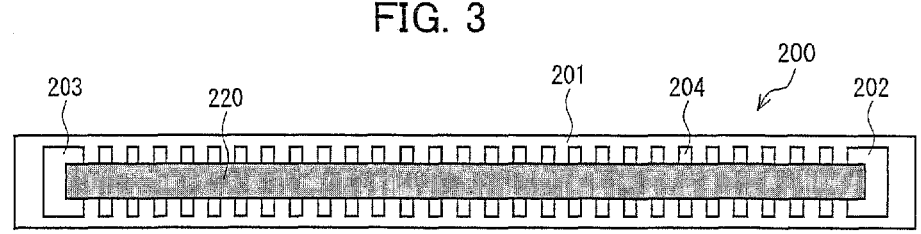
FIG. 3 is a plane view illustrating the structure of the isoelectric electrophoresis device according to an embodiment.
Figure 4:
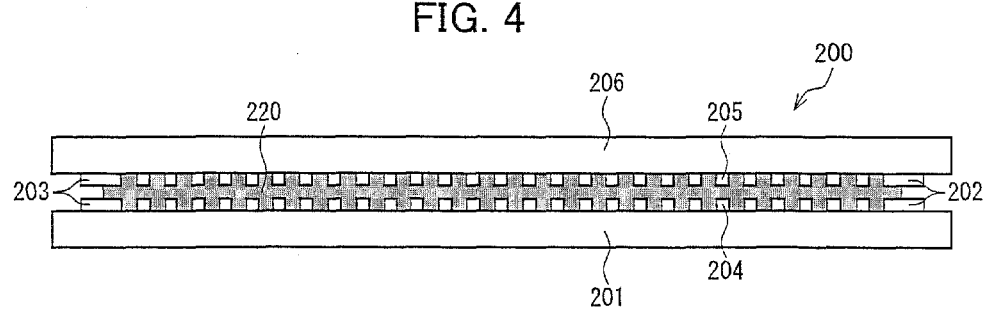
FIG. 4 is a side view illustrating the structure of the isoelectric electrophoresis device according to an embodiment.

In another embodiment, a device for electrophoresis is an isoelectric electrophoresis device. The isoelectric electrophoresis device 200 of the present embodiment is illustrated in FIG. 2 (a perspective view), in FIG. 3 (a top view), and in FIG. 4 (a side view). The isoelectric electrophoresis device 200 includes a separation chamber 201, electrodes 202 and 203 (voltage applying mean), stripe electrodes 204 and 205, and a lid member 206. Medium 220 is sandwiched between the stripe electrodes 204 and 205 in the separation chamber 201.

It is preferable that the medium 220 includes ampholyte for generating a pH gradient. When the stripe electrodes 204 and 205 apply a voltage to the medium 220, each of the electric conductors of the stripe electrodes 204 and 205 has an individual potential and an electric conductor of the stripe electrode 204 and an electric conductor of the stripe electrode 205, both of which have a same distance from respective electrodes, have a same potential. Therefore, there is a uniform potential in the vicinity of each electric conductor of the stripe electrodes 204 and 205. Accordingly, ampholyte migrates in the medium 220 and generates a uniform pH gradient.

In this case, the electrodes 202 and 203 apply a voltage so that a potential difference between each pair of electric conductors of the stripe electric conductors 213 and 214 is not more than 0.3V, thereby preventing air bubbles.

Figure 5:
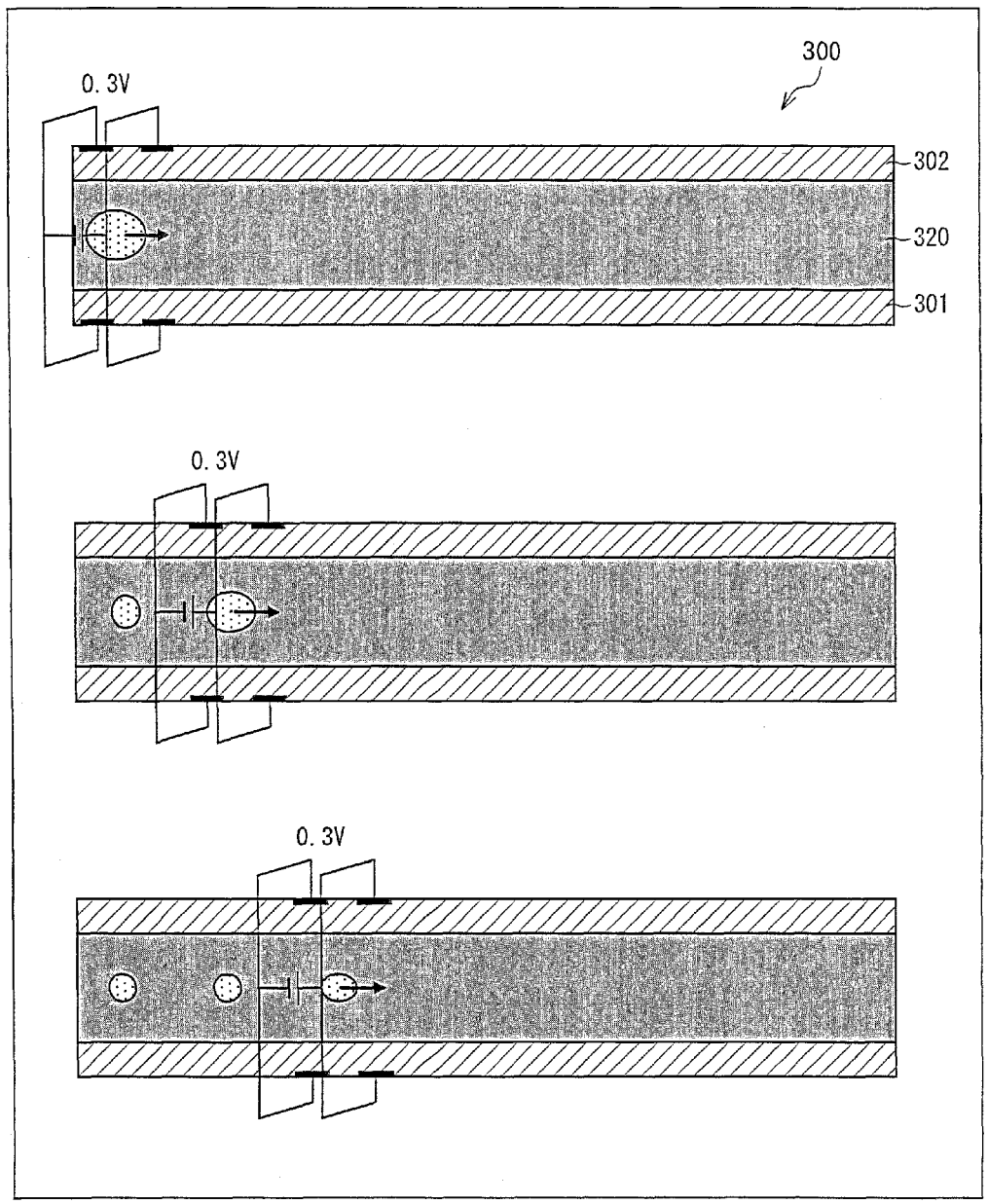
FIG. 5 is an explanatory view of an electrophoresis method according to further another embodiment.

Further, in further another embodiment, a device for electrophoresis 300 of the present invention applies a voltage to a medium 320 with use of stripe electrodes 301 and 302. FIG. 5 is an explanatory drawing of an operation of the device for electrophoresis 300 of the present embodiment. As illustrated in FIG. 5, the device for electrophoresis 300 performs electrophoresis by applying a voltage only to adjacent corresponding electric conductors of the stripe electrodes 301 and 302 and shifting the voltage applied electric conductors sequentially.

In addition to a method for applying voltage to adjacent corresponding electric conductors, it is possible to apply a few V to 10V to a plurality of electric conductors leaving a certain space and shift the voltage applied electric conductors sequentially when a gap between electric conductors is narrow. For example, in the case of 10V being applied, it is required to leave space more than 34 electric conductors. This allows applying a voltage so that the potential difference of the adjacent electric conductors is not more than 0.3V.

It is possible to prevent the generation of air bubbles by adjusting the potential difference between adjacent electric conductors 0.3V. Compared to the other embodiments, the present embodiment less likely to have a problem caused by air bubbles because a potential is applied to limited electrodes only. Needless to say, it is preferable that the potential difference between adjacent electric conductors is not more than 0.3V.

Example 1

Making a Stripe Electrode

Figure 6:
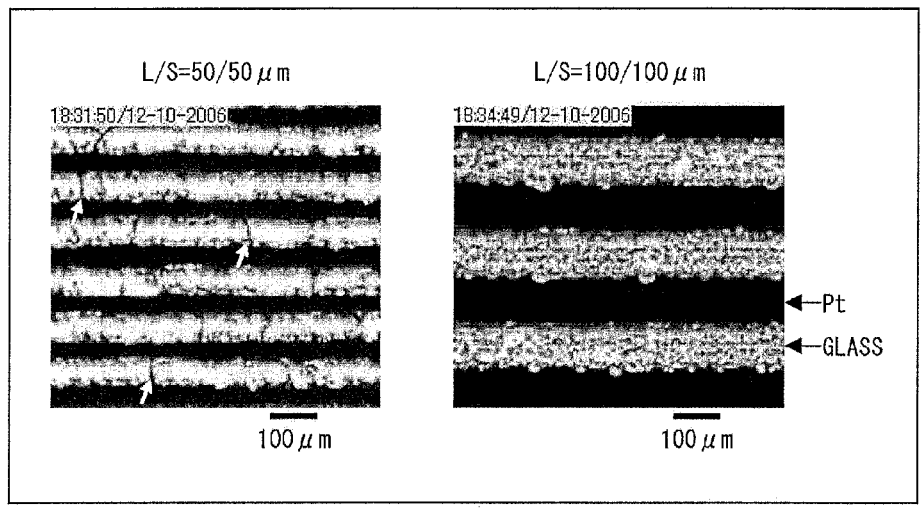
FIG. 6 is a photograph of a plurality of electric conductors according to an embodiment of the present invention.

Cr binder was deposited on a 6 cm×5 cm glass plate 3 mm in thickness by a sputtering device and about 2000 Å Pt was also deposited. Then, a thickness of Pt electrode and a gap between Pt electrodes were created to be approximately 100 μm by a Dicing saw (Disco) with a blade 100 μm in thickness. In addition, two kinds of stripe electrode substrates, (i) a thickness of Pt wire and a gap between Pt wires were 100 μm and (ii) a thickness of Pt wire and a gap between Pt wires were 50 μm, were created by a $CO_2$ laser carving machine under a following cutting condition, laser power 7%, process speed 6%, and 3000 Hz (FIG. 6). Note that the surface of the glass was little processed by a laser under the above condition.

Example 2

Comparison of Substrates

A pair of 6 cm×5 cm gel plates (glass plate) sandwiching 1 mm spacer therebetween was placed in a gel-making container. A glass substrate was used as one side of the gel plates. As for the other side of the gel plates, a stripe electrode substrate plate in which a thickness of Pt wire and a gap between Pt wires were 100 μm, a substrate whose entire surface was covered by Pt, or a glass substrate (positive control) was used.

Next, after adding a processed resolving gel solution (13% acrylamide mixture (acrylamide:bisacrylamide=29.2:0.8), 378 mM Tris-HCl (pH 8.8), 0.05% APS, and 0.1% TEMED) up to 7 mm from the tip, water was added to form a water layer thereon. After the polymerization of the resolving gel solution, the water was removed, and then the processed and concentrated resolving gel solution (4% acrylamide mixture (acrylamide:bisacrylamide=29.2:0.8), 125 mM Tris-HCl (pH 8.8), 0.05% APS, and 0.2% TEMED) was added. Then, a sample comb was placed. As for a negative electrophoresis buffer composition, 25 mM Tris, 192 mM glycine, and 0.1% SDS were used. As for a positive electrophoresis buffer composition, 150 mM Tris-HCl (pH 8.8) was used. Samples were mixed with the same amount of 0.5% agarose gel, and were injected inside a sample well. After the coagulation, SDS-PAGE was performed.

The samples to be separated by SDS-PAGE were stained and visualized by SeeBlue plus2 M. W. Marker (Invitrogen Corporation) and fluorescent-labeled DyLight fluorescent protein molecular weight marker (PIERCE).

Figure 7:
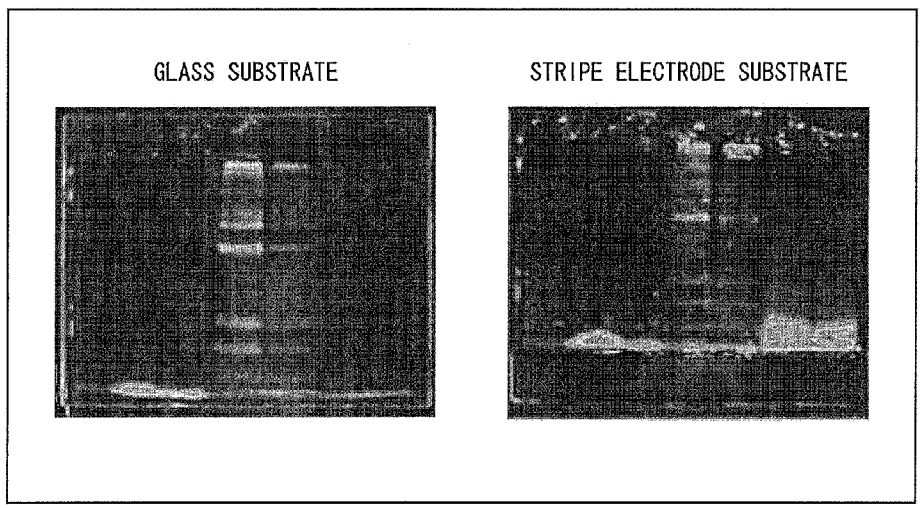
FIG. 7 is a photograph of a result of the electrophoresis method according to an embodiment.
Figure 8:
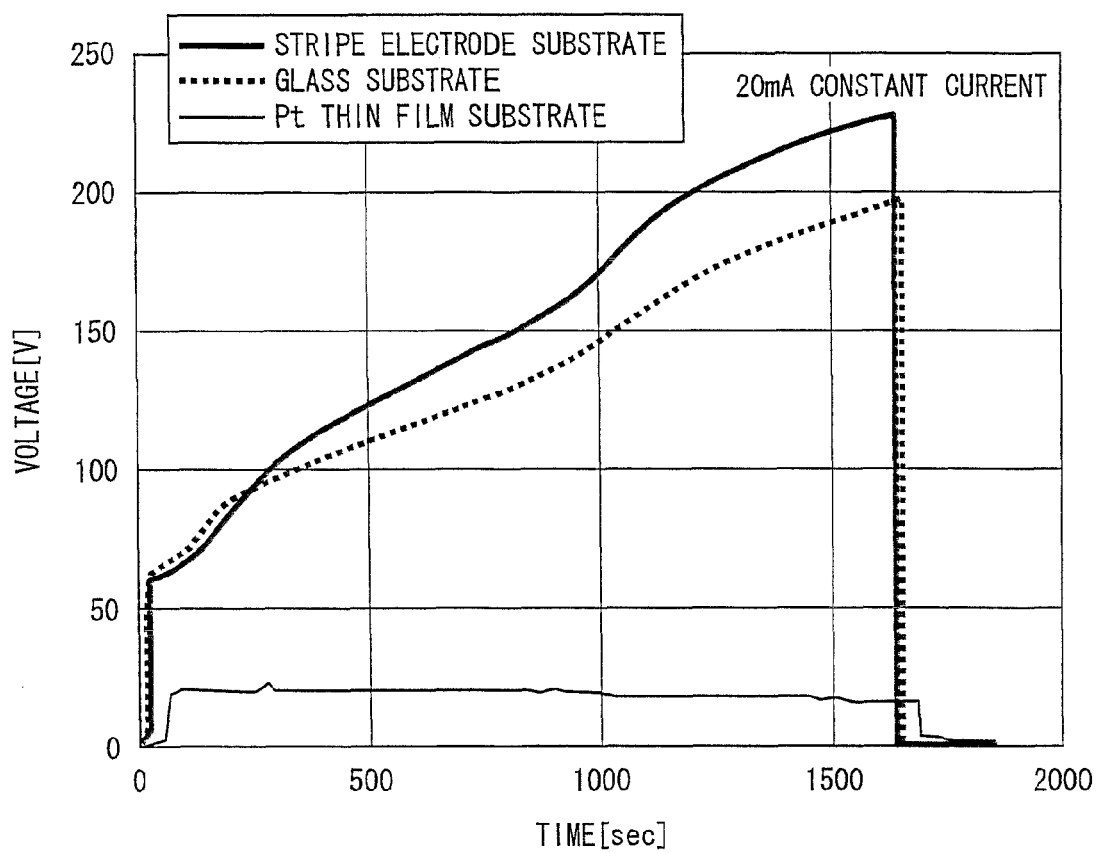
FIG. 8 is a graph of a result of the electrophoresis method according to an embodiment.

As a result of applying 20 mA constant current for 45 minutes, clear protein bands were detected even in the case where one side of the gel plates was a stripe electrode substrate (FIG. 7). On the other hand, proteins did not migrate in the case where one side of the gel plates was a substrate entirely covered with Pt. This confirmed that the voltage application was not possible in this case (FIG. 8). Also, mobility was slower in the case of using the stripe electrode substrate.

Further, in the stripe electrode, air bubbles were generated on the stripe electrode during SDS-PAGE. It was deduced that the air bubbles detached gel from the stripe electrode and buffer solution came into the gap between the gel and the stripe electrode, so that buffer action was inhibited and mobility of proteins became slow. Note that the air bubbles do not largely affect separation degree, however, the air bubbles prevent applying a uniform voltage to the stripe electrodes in the following transfer process. Thus, a method for preventing generation of air bubbles was studied.

Example 3

Studying a Method for Preventing the Generation of Air Bubbles

It was deduced that water electrolysis might occur between a pair of electrodes due to a potential difference between the electrodes (wires) of the stripe electrodes, thereby causing the air bubbles. Then, it was predicted that the generation of air bubbles could be prevented by controlling the potential difference between each pair of electrodes below 1V, decomposition voltage of water.

Then, with use of a stripe electrode substrate in which the thickness of Pt wire and the gap between Pt wires were 100 μm, the generation of air bubbles was monitored when altering applied voltage during SDS-PAGE. Table 1 shows the applied voltages, and calculated voltages between each pair of electrodes when the applied voltages were applied. Note that a voltage between a pair of electrodes was calculated by an applied voltage divided by the number of stripes.

TABLE 1

| Voltage between each pair of electrodes (V) | Air Bubbles | The Number of electrodes | Voltage | L/S (μm) | Initial Electric Currency (mA) | Device for making stripe electrode |
|---|---|---|---|---|---|---|
| 0.2 | none | 251 | 50 | 100/100 | 15 | Dicing saw |
| 0.3 | none | 251 | 75 | 100/100 | 25 | Dicing saw |
| 0.4 | generated a little | 251 | 100 | 100/100 |  | Dicing saw |
| 0.6 | generated | 251 | 150 | 100/100 | 49 | Dicing saw |
| 0.8 | generated a lot | 251 | 200 | 100/100 | 191 | Dicing saw |
| 0.3 | none | 501 | 150 | 50/50 | 56 | $CO_2$ laser carving machine |

The result shows that the air bubbles were generated when the voltage between each pair of electrodes was 0.4V or higher; and the air bubbles was not generated when the voltage was 0.3V or lower (applied voltage to gel was 75V or lower). Further, in the case where a stripe electrode substrate in which the thickness of Pt wire and the gap between Pt wires were 50 μm, the air bubbles was not generated when the applied voltage to gel was 150V (voltage between each pair of electrodes was 0.3V). Therefore, it was clear that the generation of air babbles is preventable on the condition that the voltage between each pair of electrodes is 0.3 V or lower.

Further, decomposition voltage of water is affected by a material of electrodes and components in a buffer. It is deduced that it is possible to increase an applied voltage between each pair of electrodes by using materials such as zinc or copper which have lower excessive voltage than Pt.

Example 4

Present Embodiment Worked with a Commercial Apparatus)

A stripe electrode was created by using a mini-size gel plate (10 cm×8.2 cm 3 mm in thickness Bio-Rad) in the same procedure as explained in Example 1. Five hundred stripes were created to satisfy L/S=80 μm/120 μm within 10 cm substrate. In this case, a potential difference between stripe electrodes was 0.2V. Gel was polymerized and SDS-PAGE was performed in the following three cases, (i) both sides of the gel plates were stripe electrode substrates; (ii) one side of the gel plates was a stripe electrode substrate; and (iii) both sides of the gel plates were glass substrates. SDS-PAGE was performed in a standard method by using a Mini-Protian 3 Cell (Japan Bio Lad Laboratories, Inc.) at 100V for 1 hour. Under this condition, no air bubbles were generated on the stripe electrode plate. Regardless of whether one side of the gel plates was a stripe electrode substrate, or both sides of the gel plates were stripe electrode substrates, clear-cut bands could be obtained and electrophoresis speed was not declined either.

The present embodiment makes it possible to prevent the generation of air bubbles at electric conductors inside an electrophoresis chamber and the decline in electrophoresis speed.

The present embodiment provides an improved electrophoresis technique which can be used in a filed of separating and analyzing biomaterials.

[2: Device for Electrophoresis and Transfer and Method for Electrophoresis and Transfer]

Figure 9:
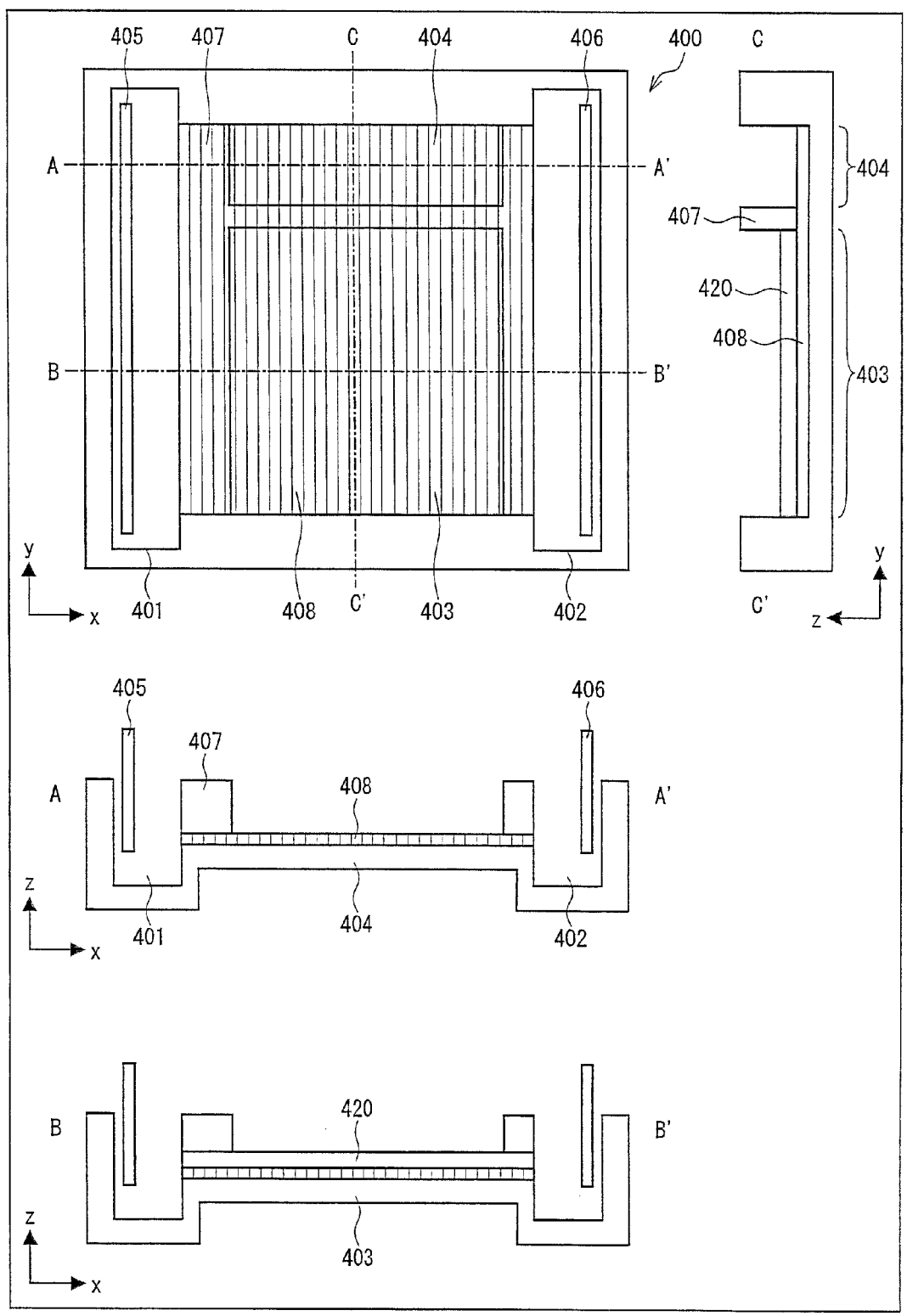
FIG. 9 is a schematic view illustrating a structure of a device for electrophoresis and transfer according to an embodiment of the present invention in electrophoresis operation.
Figure 10:
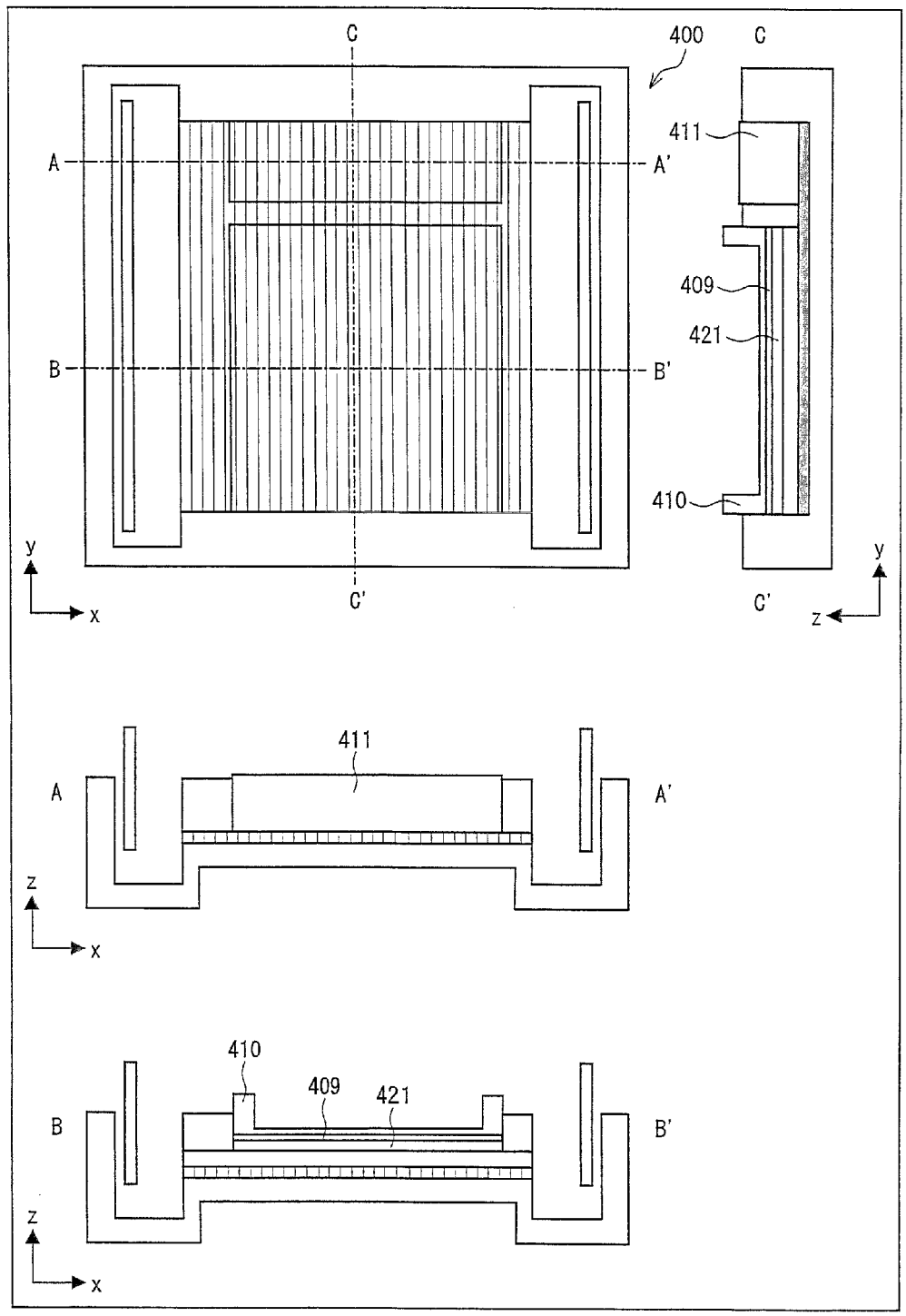
FIG. 10 is a schematic view illustrating a structure of the device for electrophoresis and transfer according to the embodiment of the present invention in transfer operation.

The following deals with an explanation of an embodiment with refer to drawings. FIG. 9 and FIG. 10 are schematic view of a device for electrophoresis and transfer 400 of an embodiment of the present invention. FIG. 9 illustrates a structure of the device for electrophoresis and transfer 400 in electrophoresis operation. FIG. 10 illustrates the device for electrophoresis and transfer 400 in transfer operation.

As illustrated in FIG. 9 and FIG. 10, the device for electrophoresis and transfer 400 includes buffer solution chambers 401 and 402, a separation section 403, a wire connecting section 404, electrodes 405 and 406 (first voltage applying means), a supporter 407, and a stripe electrode 408 (second voltage applying means, first electrode); in transfer operation, further includes electrode 409 (second voltage applying means, second electrode), a supporter 410, and a wire connector 411. The details of the stripe electrode 408 is explained later.

The buffer solution chambers 401 and 402 are used for filling a buffer solution therein. As for the buffer solution, a buffer solution which has a composition generally used for electrophoresis is available. The electrode 405 provided in the buffer solution chamber 401 has a negative potential in electrophoresis operation. The electrode 406 provided in the buffer solution chamber 402 has a positive potential in electrophoresis operation.

The stripe electrode 408 is provided on a region between the buffer solution chambers 401 and 402. Also, the region is divided into the separation section 403 and the wire connection section 404 by the holder 407. As illustrated in FIG. 9, the wire connection section 404 is isolated from buffer solution chambers 401 and 402 by the supporter 407 for preventing entering the buffer solution. Also, the upper part of the holder 407 is open so that the stripe electrode 408 located on the wire connection section 404 is able to contact with other members.

The first medium 420 including separation target components is provided on the separation section 406 and is sustained by the holder 405. The upper part of the holder 407 is open so that the first medium 420 is able to contact with other members.

The separation target components may be any components to be separated and analyzed by electrophoresis and transfer. The separation target components may be preferably prepared from a biological material such as bions, biological fluid, cell strains, cultured tissues, or fragment tissues. Polypeptide and polynucleotide are more preferable as the separation target components. As for the first medium 420, agarose gel, polyacrylamide gel, and any gel generally used for electrophoresis are available. Note that when gel is used as the first medium, a gelated first medium 420 may be placed on the separation section 406, or liquid material may be filled in the separation section 406 to be gelated there as the first medium 420 on the separation section 406. Further, when the present invention is adopted to an electrophoresis driven by a capillary electrophoresis method, a buffer solution containing polymer, which is generally used in a capillary electrophoresis method, is applicable.

In transfer operation, the stripe electrode 408 on the wire connection section 404 is conductively connected by the wire connector 411 and a negative potential is applied. Also, the holder 410 is provided on the first medium 420. The holder 410 includes the electrode 409 and the second medium 421. The first medium 420 is in contact with the second medium 421 and the electrode 409 is provided on top of them. The electrode 409 is applied a positive potential.

As for the second medium 421, materials which are able to fix the separation target components are available, and the shape is not limited but a thin membrane is preferable. Specifically, a nitrocellulose membrane, a PVDF membrane, a nylon membrane, and the like, which are used in biological macromolecule analysis technique such as a known western blotting method, are preferably used.

The stripe electrode 408 has such a structure that line-shaped electric conductors are arranged in parallel. In the device for electrophoresis and transfer 400, the stripe electrode 408 is provided in an orthogonal direction to the direction of electrophoresis. The stripe electrode 408 should be made of a conducting material which is not deteriorated even in contact with the buffer solution is preferable. Specifically, it is not limited to the following materials but the stripe electrode 408 can be made of platinum, copper, zinc, or the like. The stripe electrode 408 includes a plurality of electric conductors, and the thickness and length of each electric conductor, and the gap between conductors are not limited.

Figure 11:
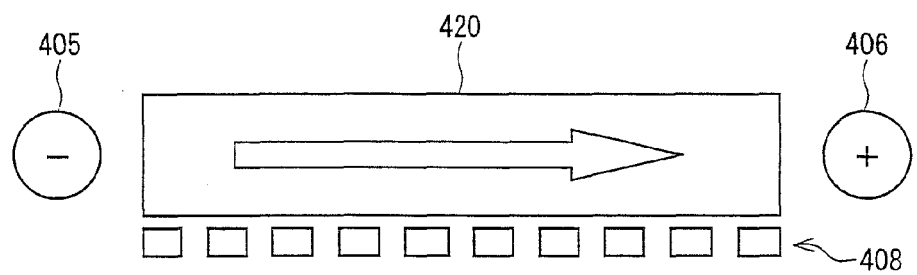
FIG. 11 is an explanatory drawing illustrating an electrophoresis operation of the device for electrophoresis and transfer according to the embodiment.
Figure 12:
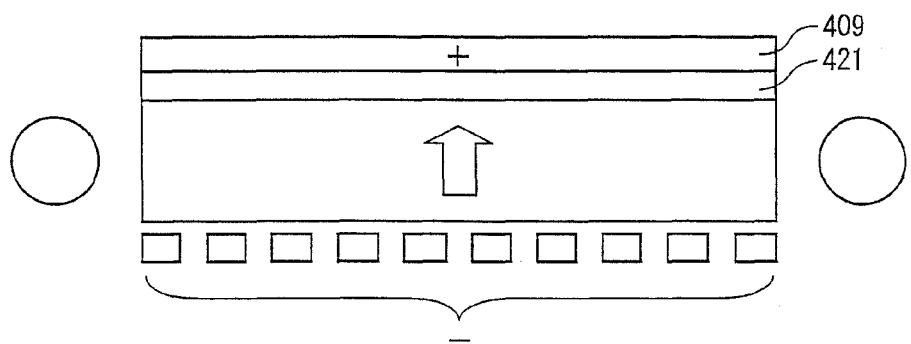
FIG. 12 is an explanatory drawing illustrating a transfer operation of the device for electrophoresis and transfer according to an embodiment.

The following explanation deals with the operation of the device for electrophoresis and transfer 400 with reference to drawings. FIG. 11 and FIG. 12 are schematic views of the device for electrophoresis and transfer 400. FIG. 11 illustrates the device for electrophoresis and transfer 400 in electrophoresis operation. FIG. 12 illustrates the device for electrophoresis and transfer 400 in transfer operation.

As illustrated in FIG. 11, since the electrode 405 has a negative potential and the electrode 406 has a positive potential during the electrophoresis operation, the separation target components in the first medium 420 migrate to the direction from the electrode 405 to the electrode 406 (a direction indicated by an arrow in FIG. 11). At this time, the stripe electrode 408 does not prevent the migration of the separation target components.

For example, as shown in another embodiment described later, if the flat-plate shaped electrode is used instead of the stripe electrode 408, a potential in the first medium 420 becomes uniform and the separation target components do not migrate.

On the other hand, the stripe electrode 408 includes a plurality of electrode regions being insulated one another and arranged in an orthogonal direction to the voltage applied direction. Therefore, a potential to the voltage applied direction never become uniform and the separation target components in the first medium 420 can migrate as explained above.

As illustrated in FIG. 12, the electrodes 405 and 406 do not apply a voltage to gel 420 in the transfer operation. The second medium 421 and the electrode 409 are provided on the first medium 420 in the transfer operation. As a negative potential is applied to the stripe electrode 408 and a positive potential is applied to the electrode 409, the separation target components in the first medium 420 migrate from the stripe electrode 408 to the electrode 409 (direction toward the second medium 421). This allows the separation target components to be transferred to the second medium 421.

A known and commonly used method can be used for switching potentials of the electrodes 405, 406, and 409 between the electrophoresis operation and transfer operation. As described before, the switching the potential of the stripe electrode 408 is carried out by connecting or disconnecting the wire connector 411 to the stripe electrode 408 on the wire connection section 404. However, the switching is not limited to this way. Any methods to apply a negative potential to the stripe electrode 408 are applicable, for example, a known circuit technique such as a switch may be adopted.

The applied voltage in the electrophoresis and transfer operation may be a voltage which is used for general electrophoresis devices and transfer devices. A known and commonly used technique can be used as a voltage applying means other than the above explained part.

In the device for electrophoresis and transfer 400 of an embodiment, the second medium 421 can be detached easily as explained before. Therefore, the analysis (such as antibody-antigen reaction) with use of the second medium 421 including transferred target components is favorably performed.

Figure 13:
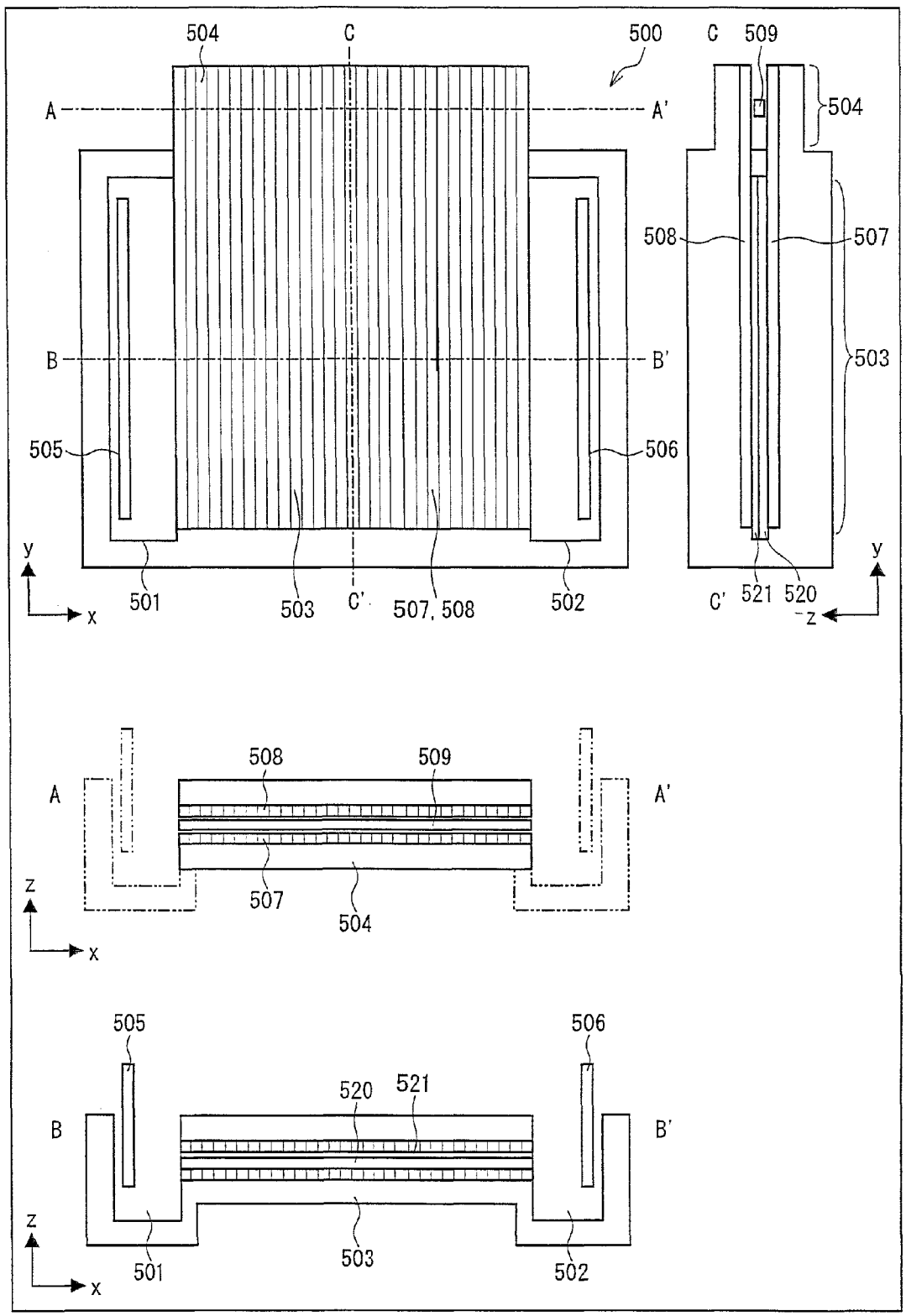
FIG. 13 is a schematic view illustrating another structure of a device for electrophoresis and transfer according to an embodiment.

The following explanation deals with another embodiment of the device for electrophoresis and transfer with reference to the drawings. FIG. 13 is a schematic view of a device for electrophoresis and transfer 500 of the present embodiment.

As illustrated in FIG. 13, a device for electrophoresis and transfer 500 includes a buffer solution chambers 501 and 502, a separation section 503, a wire connection section 504, electrodes 505 and 506 (first voltage applying means), stripe electrodes 507 and 508 (second voltage applying means, first and the second electrodes), and a wire connector 509.

The separation section 503 is provided between the buffer solution chambers 501 and 502, and holds the first medium 520 and the second medium 521 by sandwiching them. The wire connection section 504 is provided at an outer region between the buffer solution chambers 501 and 502, and adjacent to the separation section 503. In the area from the separation section 503 to the wire connection section 504, the stripe electrodes 507 and 508 are provided one above the other and hold the first medium 520 and the second medium 521 therebetween at the separation section 503.

The explanation of the buffer solution chambers 501 and 502, the electrodes 505 and 506, the first medium 520, the second medium 521, and the stripe electrodes 507 and 508 are the same as the explanation of the device for electrophoresis and transfer 400 above mentioned.

Figure 14:
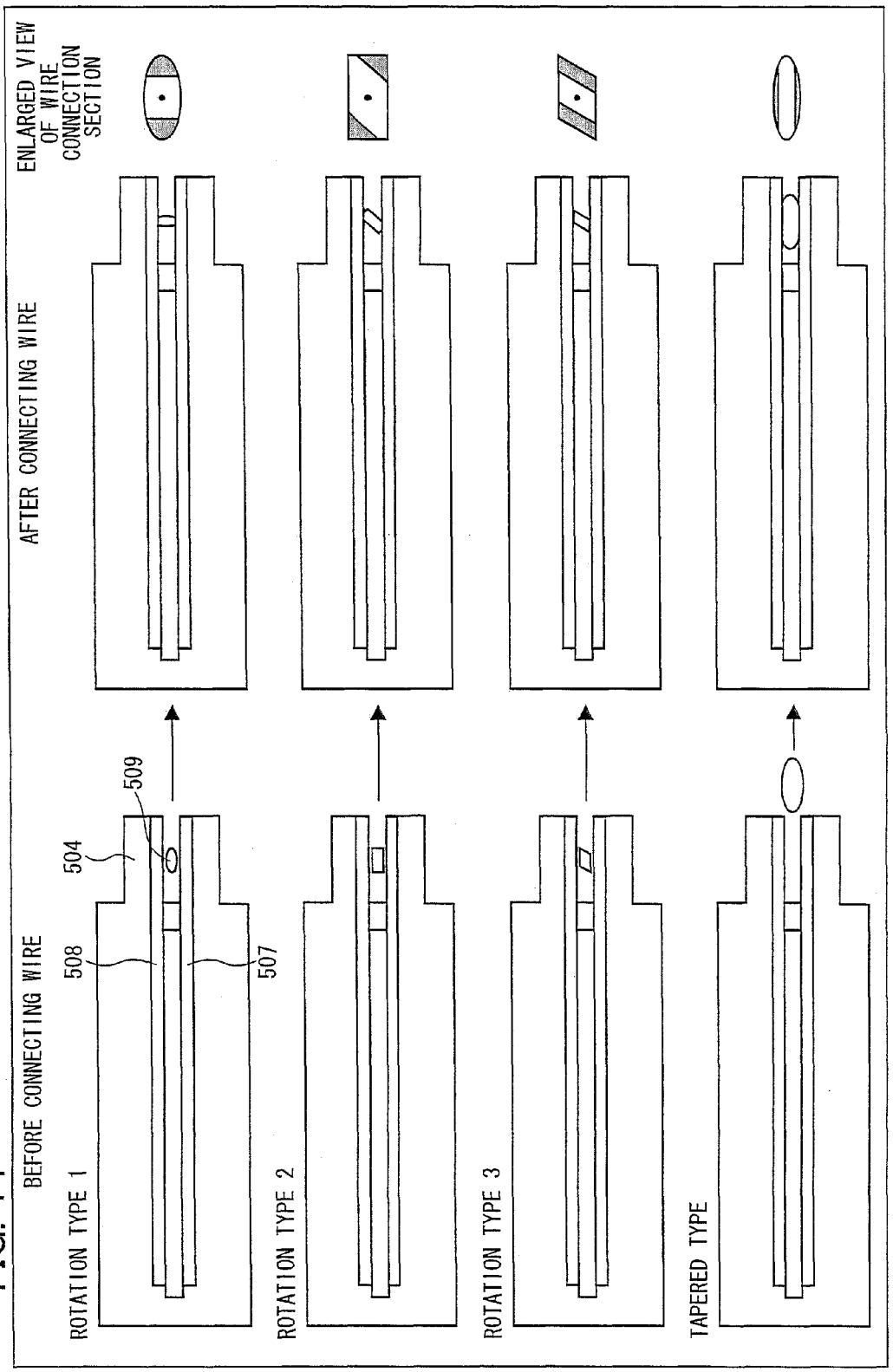
FIG. 14 is an explanatory view illustrating an operation of a wire connector in the device for electrophoresis and transfer according to an embodiment.

The wire connector 509 is a part for applying a voltage to the stripe electrodes 507 and 508 in transfer operation. FIG. 14 is an explanatory drawing illustrating a mechanism how the wire connector 509 applies a potential to the stripe electrodes 507 and 508. As illustrated in enlarged views in FIG. 14, the wire connector 509 includes two separated regions (shaded areas in the drawings) which are connected to not illustrated voltage supply means (such as a power supply) having positive and negative potentials, respectively. The wire connector 509 rotates in the wire connection section 504 (rotation types 1 to 3 in the figure); or the wire connector 509 is inserted between the stripe electrodes 507 and 508 (a tapered type in the figure). This allows the above regions to connect the stripe electrodes 507 and 508 for applying a positive potential and a negative potential, respectively. Note that the present invention is not limited to the method above for applying the positive potential and the negative potential to the stripe electrodes 507 and 508, respectively. For example, a known circuit technology such as a switch may be adopted.

Figure 15:
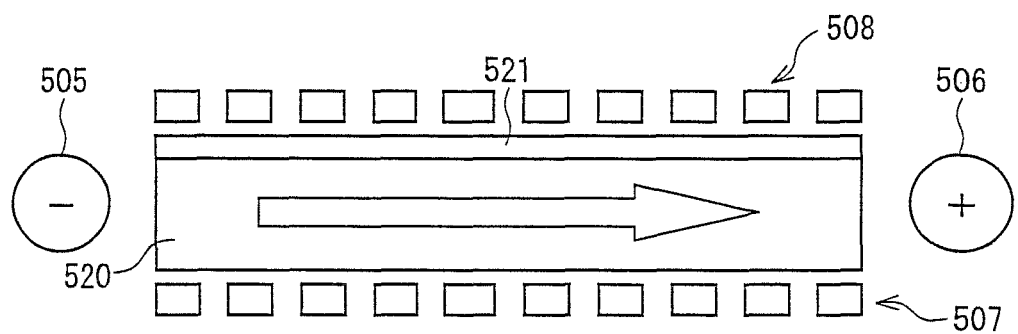
FIG. 15 is an explanatory view illustrating an electrophoresis operation of the device for electrophoresis and transfer according to an embodiment.
Figure 16:
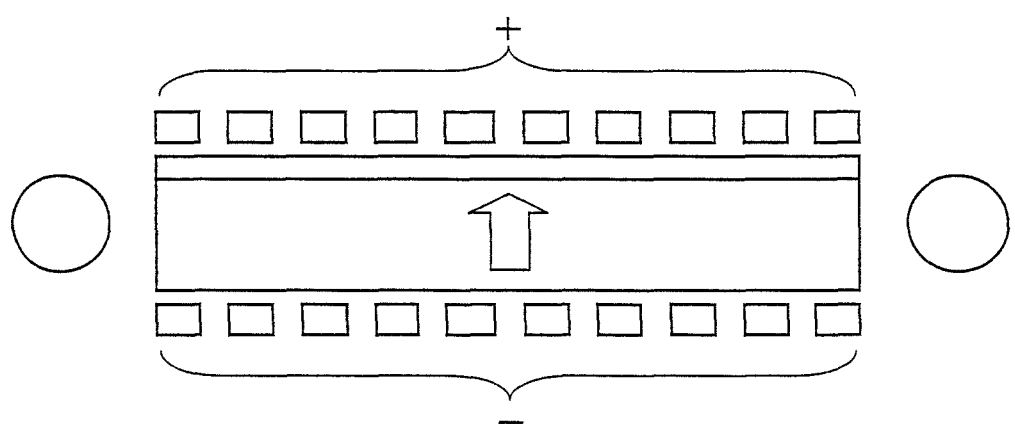
FIG. 16 is an explanatory view illustrating a transfer operation of the device for electrophoresis and transfer according to an embodiment.

The following explanation deals with an operation of the device for electrophoresis and transfer 500 with reference to drawings. FIG. 15 and FIG. 16 are schematic views of the device for electrophoresis and transfer 500. FIG. 15 illustrates the device for electrophoresis and transfer 500 in the electrophoresis operation. FIG. 16 illustrates the device for electrophoresis and transfer 500 in the transfer operation.

As illustrated in FIG. 15, the electrode 505 has a negative potential and the electrode 506 has a positive potential in electrophoresis operation. Therefore, separation target components in the first medium 502 migrate in a direction from the electrode 505 to the electrode 506 (direction indicated by an arrow in FIG. 15). At this time, the stripe electrodes 507 and 508 do not prevent the migration of the separation target components as described before.

As illustrated in FIG. 16, in the transfer operation, while the electrodes 505 and 506 do not apply a voltage to the first medium 520, the negative potential is applied to the stripe electrode 507 and the positive potential is applied to the stripe electrode 508. Accordingly, the separation target components in the first medium 520 migrate in a direction from the stripe electrode 507 to the stripe electrode 508 (direction indicated by an arrow in FIG. 16). This allows the separation target components to be transferred to the second medium 521.

The explanation above deals with the case where the first medium is provided on the negative stripe electrode 507 side and the second medium is provided on the positive electrode 508 side. The present invention, however, may be oppositely configured such that the first medium is provided on the positive electrode 508 side and the second medium are provided is provided on the negative stripe electrode 507 side.

Figure 17:
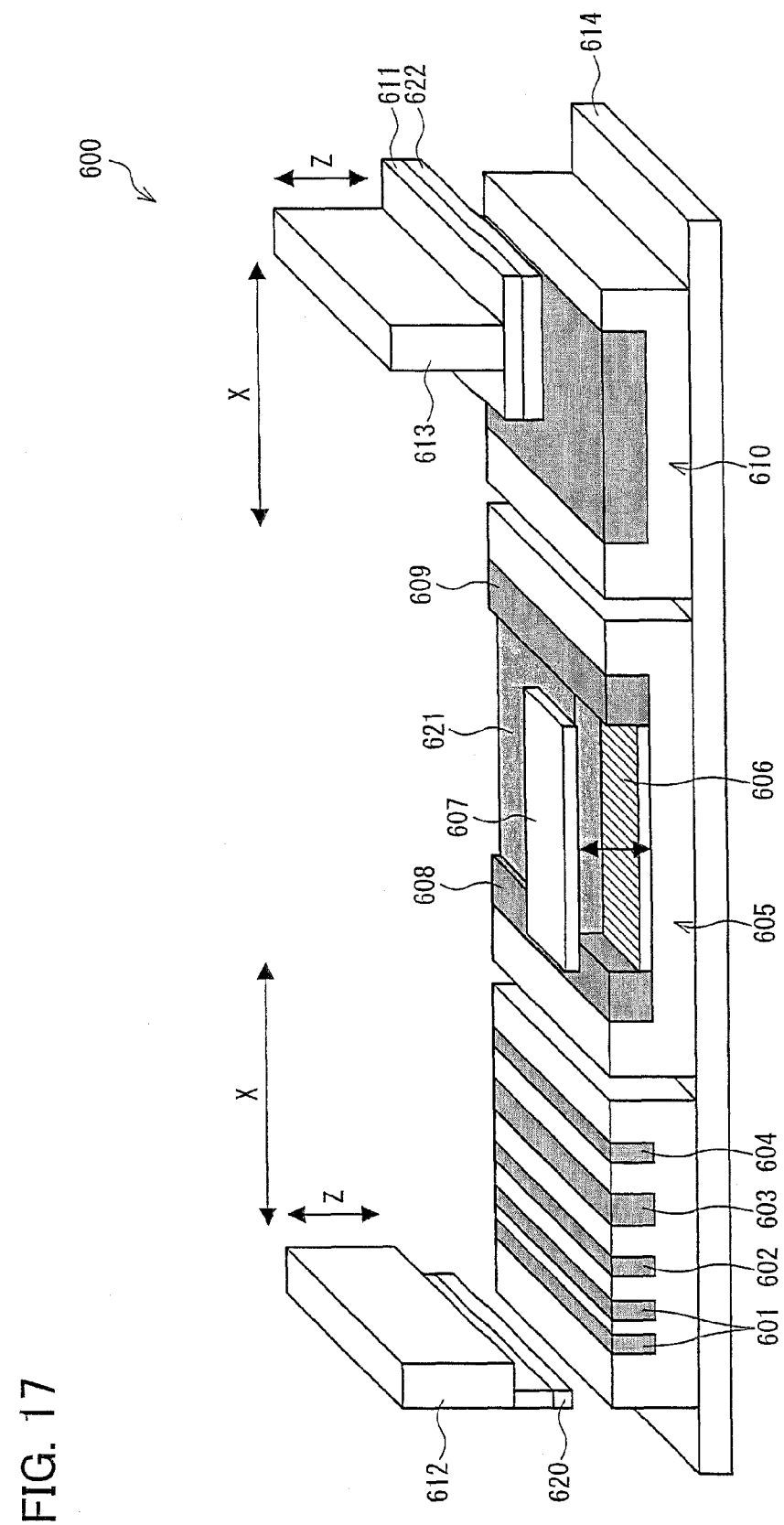
FIG. 17 is a schematic view illustrating a structure of an automated two-dimensional Western blotting device according to an embodiment.

The present invention also provides an automated two-dimensional electrophoresis—western blotting device (2 DGE-WB) including the device for electrophoresis and transfer of the present embodiment. FIG. 17 is a schematic view of the 2 DGE-WB device as an embodiment in accordance with the present invention.

As illustrated in FIG. 17, the 2 DGE-WB device 600 includes a base material 614, a sample injection and swelling chamber 601, an isoelectric electrophoresis chamber 602, an SDS equilibrium chamber 603, gel storage for isoelectric electrophoresis 604, an electrophoresis and transfer section 605 (device for electrophoresis and transfer), a stripe electrode for transfer 606 (second voltage applying means, first electrode), a wire connection member 607, a buffer liquid chambers 608 and 609, a reaction chamber 610, an electrode for transfer 611 (second voltage applying means, second electrode), and supporting members 612 and 613. A gel for an isoelectric electrophoresis 620 is placed in the gel storage for an isoelectric electrophoresis 604, and a gel for two-dimensional electrophoresis 621 is placed in the electrophoresis and transfer section 605. The supporting member 613 has a transfer base material 622 at a bottom part of the electrode for transfer 611.

The supporting member 612 performs as follows, (i) obtaining gel for an isoelectric electrophoresis 620 from the gel storage for isoelectric electrophoresis 604; (ii) carrying the obtained gel for an isoelectric electrophoresis 620 to the sample injection and swelling chamber 601 and performing sample injection and swelling; (iii) performing isoelectric electrophoresis to separate the samples injected in the gel for an isoelectric electrophoresis 620 in the isoelectric electrophoresis chamber 602; (iv) SDS equilibrating the gel for the isoelectric electrophoresis 620 including separated samples in the SDS equilibrium chamber 603 and carrying the SDS equilibrated gel to the electrophoresis and transfer section 605 for contacting the gel for two-dimensional electrophoresis 621; (v) performing the two-dimensional electrophoresis in the electrophoresis and transfer section 605; (vi) transferring the samples from the gel for two-dimensional electrophoresis 621 to the a transfer base material 622 in such a manner that the transfer electrode 611 and the transfer base material 622 were placed on the gel for two-dimensional electrophoresis 621 by the supporting member 613, and the stripe electrode for transfer 606 and connection member 607 are connected with a wire; (vii) the supporting member 613 carrying the transfer material 622 including transferred samples to the reaction chamber 610 and carrying out an antigen antibody reaction.

As explained above, since the 2 DGE-WB device 600 of the present embodiment including the device for the electrophoresis and transfer of the present embodiment, the same members can be used in the processes of two-dimensional electrophoresis and transfer. Therefore, it is not necessary to carry the gel for two-dimensional electrophoresis 621. This allows the two-dimensional electrophoresis and western blotting to be performed continuously and favorably.

The present embodiment further provides a chip for electrophoresis and transfer which is implemented in the device for electrophoresis and transfer of the present invention. The chip for electrophoresis and transfer of the present embodiment includes a separation section for placing the first medium including separation target components and a second medium in contact with the first medium, a first buffer solution chamber and a second buffer solution chamber sandwiching the separation section, and a first electrode having a plurality of electrode regions being insulated one another and arranged in a specific direction specified by the first buffer solution chamber and the second buffer liquid chamber. In this specification, a structure as described above, which includes a separation section, a first and second buffer solution chambers, and a first electrode, is called a chip for electrophoresis and transfer.

The chip for electrophoresis and transfer of the present embodiment is capable of separating separation target components in the first medium in the above mentioned direction by placing electrodes in the first and the second buffer solution chambers and applying a voltage to the first medium located on the separation section. Each of the electric regions in the first electrode located on the separation section are arranged in the above mentioned direction and are insulated one another. Therefore, the electric regions do not affect the separation of the target components.

It is easy to understand for a skilled person in the art that the above-mentioned chip for electrophoresis and transfer is easily implemented to the device for electrophoresis and transfer of the present embodiment. Since the chip of the present embodiment includes the separation section, the first and the second buffer solution chambers, and the first electrode, it is possible to create, for example, a device similar to the device for electrophoresis and transfer 400 of an embodiment in accordance with the present invention by implementing the chip to a device including an electrode for electrophoresis which may be placed in the first and the second buffer solution chambers and an electrode for transfer which may be placed in the upper part of the separation section.

Note that the chip for electrophoresis and transfer of the present embodiment may be implemented in a device for electrophoresis including first voltage applying means in electrophoresis operation, or may be implemented in a device for transfer including second voltage applying means in transfer operation. The chip for electrophoresis and transfer is capable of having the first medium and is easy to be carried between a device for electrophoresis and a device for transfer.

Reference Example 1

Electrophoresis without One Side of the Gel Plates

Electrophoresis was performed by using the device for electrophoresis and transfer 400 of an embodiment on the condition that one side of the gel plates was removed. Before studying the device for electrophoresis and transfer of the present embodiment, a conventional electrophoresis device was investigated whether it was able to perform electrophoresis or not on the condition that one side of the gel plates was removed.

Figure 18:
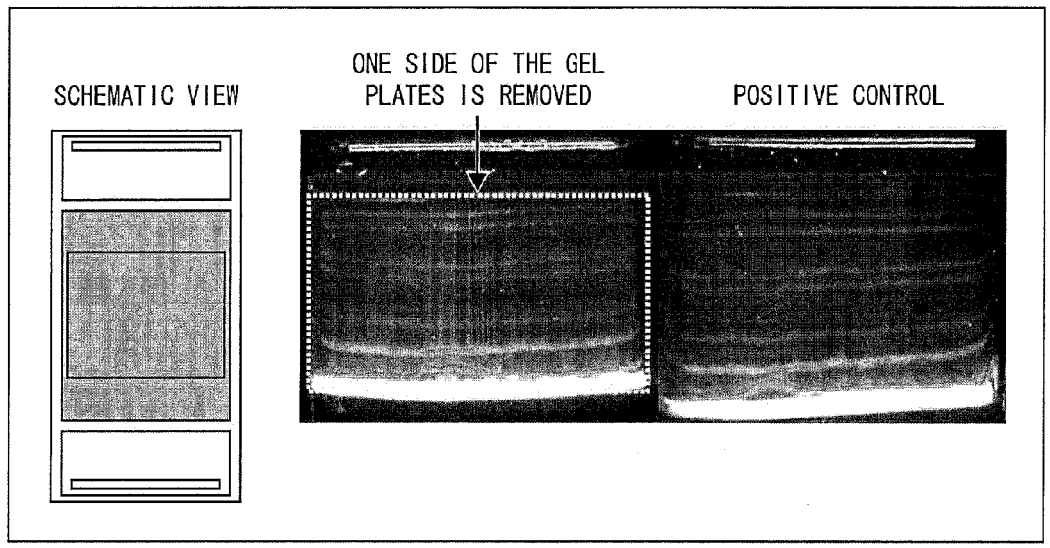
FIG. 18 is a photograph showing a result of electrophoresis in the case where one side of the gel plates is removed.
Figure 19:
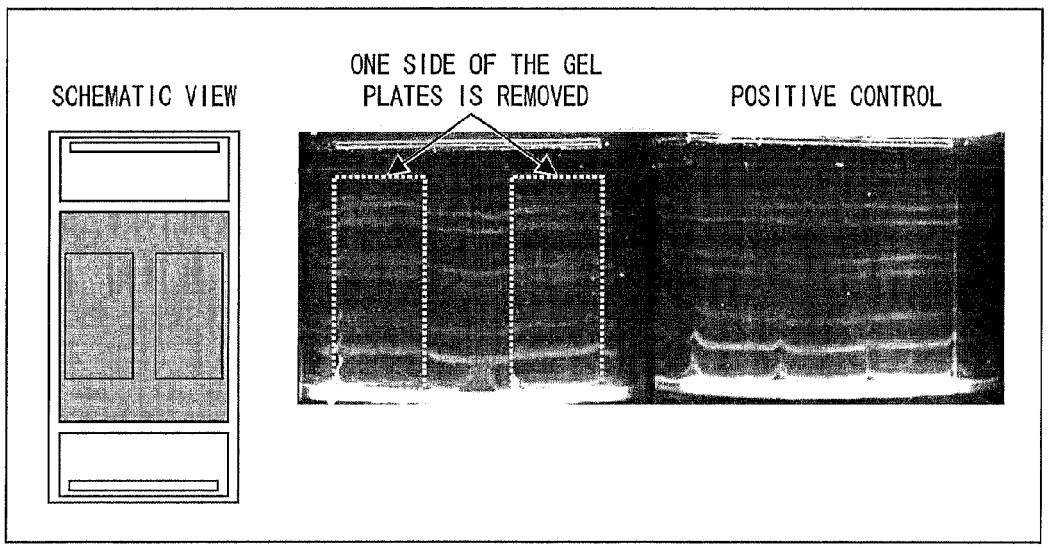
FIG. 19 is a photograph showing another result of electrophoresis in the case where one side of the gel plates is removed.

As illustrated in FIG. 18 and FIG. 19, as is the case with having both gel plates, it was possible to obtain a protein separation result even though one side of the gal plates was removed.

The reason why the electrophoresis device without one side of the gel plates obtained bands of separated proteins which were not clear enough is considered that the separated proteins are trapped in the polyacrylamide gel (PAG) due to the dryness of the surface of the gel during SDS-PAGE. Therefore, it is preferable to have a moisture control.

Example 5

Creation of a Stripe Electrode

According to Reference Example 1, it was clear that electrophoresis was able to be performed without one side of the gel plates. Therefore, further study was preceded.

After Cr binder was deposited on a 6 cm×5 cm glass plate 3 mm in thickness by a sputtering device and about 2000 Å Pt was also deposited. Then, a thickness of Pt and a gap between Pt electrodes were created to be approximately 100 µm by a Dicing saw (Disco) with a blade 100 µm in thickness. In addition, two kinds of stripe electrode substrates, (i) a thickness of Pt wire and a gap between Pt wires were 100 µm and (ii) a thickness of Pt wire and a gap between Pt wires were 50 µm, were created by a $CO_2$ laser carving machine under a following cutting condition, laser power 1.75 W, process speed 10.8 cm/sec, and pulse cycle 3000 Hz (FIG. 6). Note that the surface of the glass was little processed by a laser under the above condition.

Example 6

Comparison of the Substrates

A pair of 6 cm×5 cm gel plates (glass plate) sandwiching 1 mm spacer therebetween was placed in a gel-making container. A glass substrate was used as one side of the gel plates. As for the other side of the gel plates, a stripe electrode substrate plate in which a thickness of Pt wire and a gap between Pt wires were 100 µm, a substrate whose entire surface was covered with Pt, or a glass substrate (positive control) was used.

Next, after adding a processed resolving gel solution (13% acrylamide mixture (acrylamide:bisacrylamide=29.2:0.8), 378 mM Tris-HCl (pH 8.8), 0.05% APS, and 0.1% TEMED) up to 7 mm from the tip, a layer of water was formed thereon. After the polymerization of resolving gel solution, the water was removed, and then the processed and concentrated resolving gel solution (4% acrylamide mixture (acrylamide:bisacrylamide=29.2:0.8), 125 mM Tris-HCl (pH 8.8), 0.05% APS, and 0.2% TEMED) was added, followed by a sample comb placement. As for a negative electrophoresis buffer composition, 25 mM Tris, 192 mM glycine, and 0.1% SDS were used. As for a positive electrophoresis buffer composition, 150 mM Trus-HCl (pH 8.8) was used. Samples were mixed with the same amount of 0.5% agarose gel, and were introduced in sample wells. After the coagulation, SDS-PAGE was performed.

The samples to be separated by SDS-PAGE were stained and visualized by SeeBlue plus2 M. W. Marker (Invitrogen Corporation) and fluorescent-labeled DyLight fluorescent protein molecular weight marker (PIERCE).

As a result of applying 20 mA currency for 45 minutes, clear protein bands were detected in the case where one side of the gel plates was a stripe electrode substrate (FIG. 7). On the other hand, proteins did not migrate in the case where one side of the gel plates was the substrate entirely covered with Pt. This confirmed that the voltage application was not possible in this case (FIG. 8).

Example 7

Study of Protein Transfer with Use of a Chip

The present inventors studied whether a series of procedures from SDS-PAGE to transfer is able to be performed in the same chip by using an own device in which an electrophoresis chamber and a chip-like gel plate whose one side of gal surface was empty were separated each other.

Figure 20:
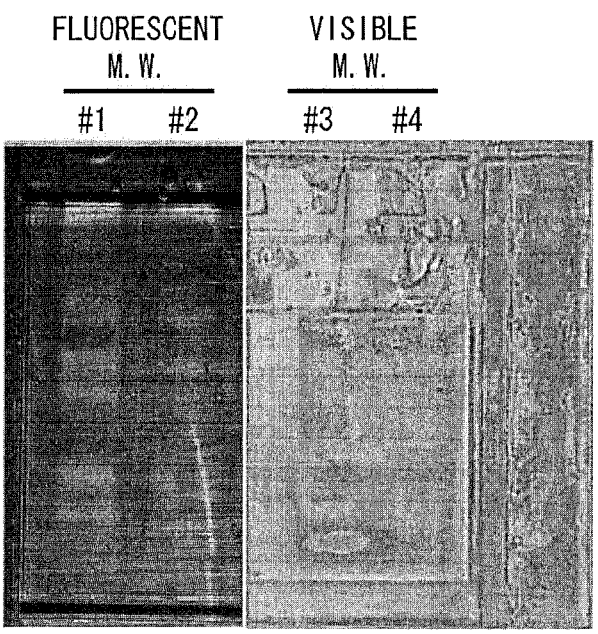
FIG. 20 is a photograph of the device for electrophoresis and transfer according to the embodiment of the present invention which was taken right after an electrophoresis operation.
Figure 21:
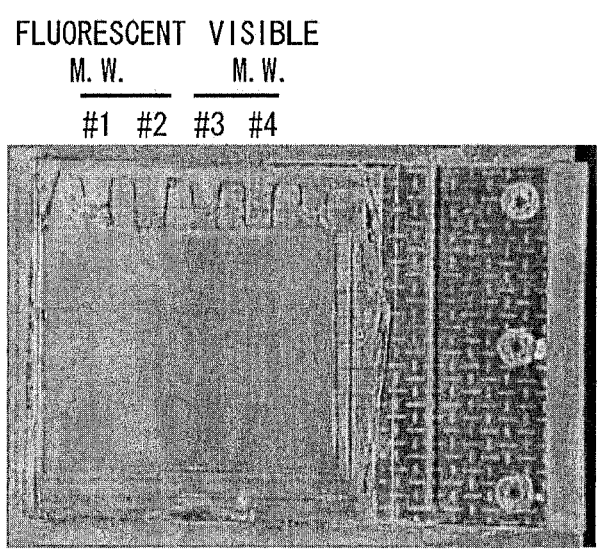
FIG. 21 is a photograph of the device for electrophoresis and transfer according to an embodiment which was taken after a transfer operation.
Figure 22:
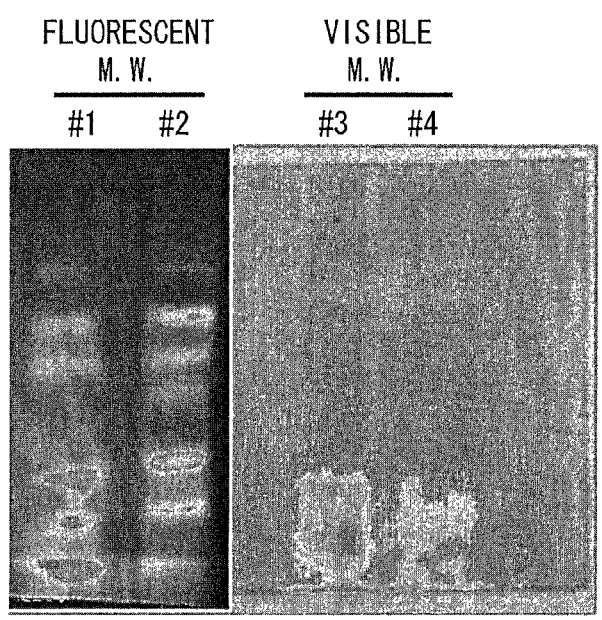
FIG. 22 is a photograph of a transferred membrane of the device for electrophoresis and transfer according to an embodiment which was taken right after a transfer operation.

After the proteins were separated by SDS-PAGE, the separated proteins were transferred with use of a stripe electrode substrate in which a thickness of Pt wire and a gap between Pt wires were 100 μm as a negative electrode and a stainless plate as a positive electrode. FIG. 20 is a photograph of a chip right after performing SDS-PAGE, and FIG. 21 is a photograph of the chip after a transfer. FIG. 22 is a photograph of a transfer membrane (Immobilon-FL, PVDF membrane). The separation and transfer of proteins was performed, as shown in those photographs. As above explained, it was confirmed that a series of procedures from SDS-PAGE to transfer was able to be performed in one chip without removing gel from gel plate.

Figure 23:
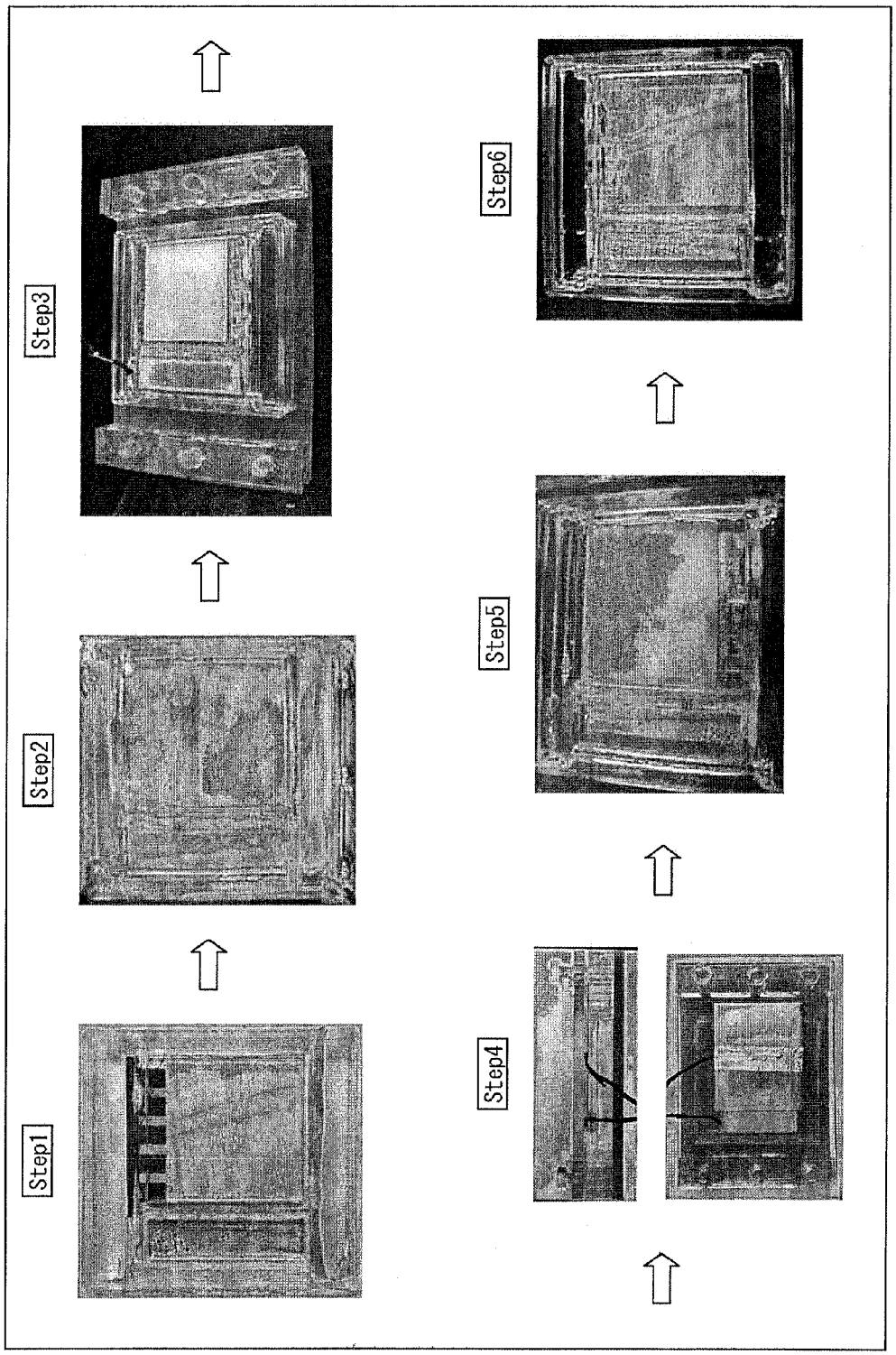
FIG. 23 is a photograph of a series of procedures of a method for electrophoresis and transfer according to the embodiment.

FIG. 23 is a plurality of photographs showing each of the processes. Step 1 is a photograph of filling gel in a chip with a stripe electrode. Step 2 is a photograph of performing SDS-PAGE. Step 3 is a photograph showing that the chip was placed in a transfer cassette (a device for applying a voltage for transfer to the chip) and a PVDF membrane was placed. Step 4 is a photograph of setting a positive electrode. Step 5 is a photograph of removing the positive electrode after a transfer. Step 6 is a photograph after removing (obtaining) the PVDF membrane.

Example 8

Study of a Structure of Stripe Electrodes Sandwiching Gel

Polyacrylamide gel electrophoresis (PAGE) was performed by using a chip in which stripe electrodes were provided on both sides of the chip and a PVDF (polyvinylidene fluoride) membrane and gel were provided. The following is an assessment of the effects of the stripe electrodes and PVDF membrane on an electrophoresis pattern.

The stripe electrode was an electrode prepared by depositing Platinum on a 50 mm×60 mm crystal glass by photolithography to create 50 μm-thick Pt wires repeated 500 times with 50 μm intervals. As for a PVDF membrane, Immobilon FL made by Millipore Corporation was used. As for a gel forming condition, the concentrated gel was formed in 4% acrylamide density and resolving gel was formed in 13% acrylamide density, both of which were gel 1 mm in thickness. As for electrophoresis test samples, a molecular weight marker SeeBlue Pre-stained made by Invitrogen Corporation was used.

On the base plate of the chip made of polymethyl methacrylate, a stripe electrode with the electrode plane facing upward, a PVDF membrane, a spacer glass in 1 mm thickness, and a stripe electrode with the electrode plane facing downward were layered in this order; and a chip lid covered on top. Acrylamide monomer liquid filled the space in 1 mm thickness to form a concentrated gel and a resolving gel. Then, an electrophoresis was performed at 150V after injecting samples.

Figure 24:
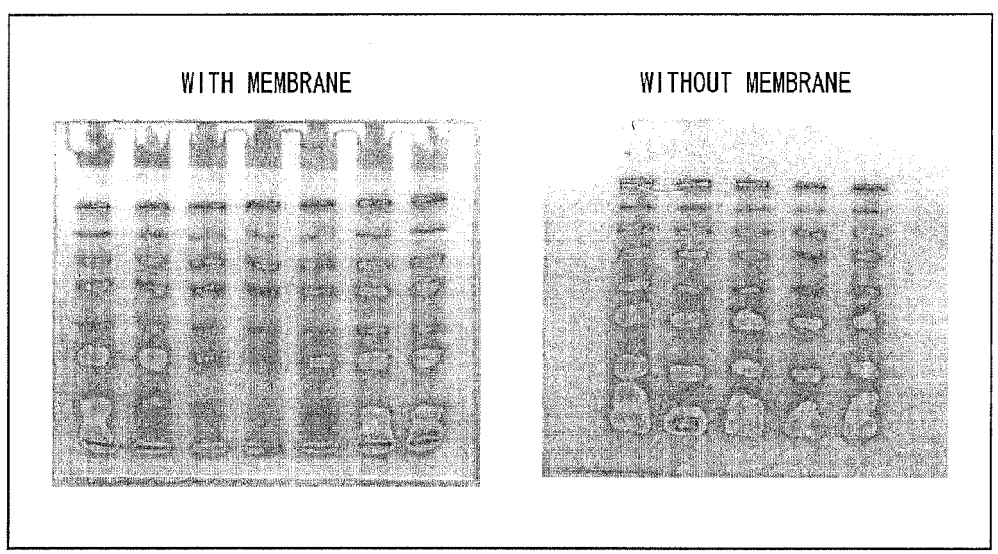
FIG. 24 is a photograph showing a result of a transfer performed by the device for electrophoresis and transfer according to an embodiment.

FIG. 24 shows the result thereof. As illustrated in FIG. 24, in the polyacrylamide gel electrophoresis performed by the chip in which the stripe electrodes were located on both sides of the chip respectively and the PVDF membrane was placed, it was able to obtain a separation pattern as in the case with a separation pattern without a PVDF membrane.

The present embodiment allows performing both electrophoresis and transfer without removing gel. Therefore, it is possible to provide a practical and easy-to-use device for electrophoresis and transfer.

The present embodiment allows providing a practical and easy-to-use device for electrophoresis and transfer. For example, a series of procedures from SDS-PAGE to Western blotting can be preformed by one chip. Further, it is possible to provide an automated two-dimensional electrophoresis—western blotting device in combination with two-axis carrier type automation device.

[3: Device for Transfer and Method for Transfer]

Transfer of proteins is carried out in a vertical direction to the direction of migration in electrophoresis. It is difficult to uniformly transfer the separated protein after electrophoresis because its molecular weight varies from several hundred kD to several kD.

In SDS-PAGE or agarose gel electrophoresis, smaller molecular weight proteins migrate further due to an effect of molecular screening. Therefore, when a cytolytic liquid is separated by these electrophoresis, bands are emerged on a surface of gel in decreasing order of molecules weight, each band being formed with proteins having the same molecular weight. For example, when performing SDS-PAGE with use of 12% acrylamide polyacrylamide gel, proteins are able to be separated and classified into about 200 kD to several kD molecules weight as a plurality of bands.

In transferring proteins separated into each molecular weight, when the target transfer proteins are small or medium sized molecular weights, it is possible to be transferred in short period of time from 30 to 60 minutes. However, it takes more than 60 minutes in transferring high molecular weight proteins. Also, longer period transfer requires more SDS in buffer, so SDS is required to be added during a transfer buffer. SDS increases transfer efficiency, however, causes the following problems. The obtained protein bands after transfer are not clear enough. Low molecular weight protein in transfer base material becomes unstable and passes through the transfer base material.

The device for transfer of the present embodiment enables to adjust voltage condition, transfer duration, and electric currency condition depending on a molecular weight of each protein for transferring proteins of various molecular weight from gel to a transfer substrate simultaneously and efficiently.

Namely, the device for transfer of the present embodiment applies a voltage to the first medium in such a manner that a certain position and another position in the first medium are provided different voltages or different voltage durations.

Further, in an embodiment of the device for transfer, a voltage applied to a certain position in the first medium is the same as a voltage applied to another position which is posteriorly-located from the certain position in a specific direction specified by the first medium, or higher. Namely, the above device for transfer increases a voltage applied to the first medium stepwise or gradually in the specific direction specified by the first medium.

Also, in another embodiment of the device for transfer, a voltage duration applied to a certain position in the first medium is the same or longer to that of another position located in upstream of the certain position with regard to the specific direction specified by the first medium. Namely, the above device for transfer increase a voltage duration applied to the first medium stepwise or gradually with respect to the specific direction specified by the first medium.

The following explanation deals with embodiments in details with reference to the drawings.

Figure 25:
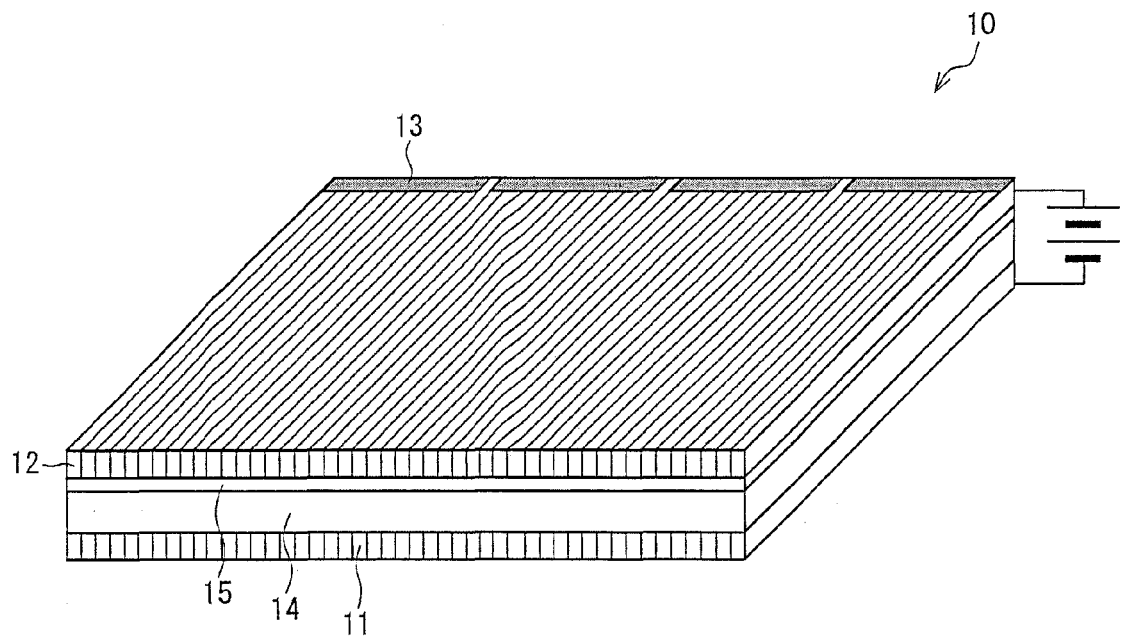
FIG. 25 is a perspective view illustrating an overall of a device for transfer according to an embodiment.

FIG. 25 is a perspective view illustrating an overall of a device for transfer 10 according to an embodiment. The device for transfer 10 of the present embodiment includes stripe electrodes 11 and 12 (voltage applying means), a conductive path 13, and is capable of having a first medium 14 and a second medium 15.

The first medium 14 is not limited and any mediums including target transfer components are preferably used, such as agarose gel, polyacrylamide gel, and the like which are generally used for electrophoresis. The target transfer components are not limited and biological materials such as bion, biological fluid, cell strains, cultured tissues, and fragment tissues are preferably used. More preferably, polypeptide or polynucleotide is used as the target transfer components. The second medium 15 should be a material which can hold the transferred transfer target components, and the form is not limited but a form like a thin membrane is preferable. Specifically, a nitrocellulose membrane, a PVDF membrane, and a nylon membrane, which are generally used for biopolymer analysis such as a known western blotting method, are preferably used as the second medium 15. Also, the second medium is provided in contact with the first medium. The above explanation about the first and the second mediums are applicable to the following embodiments.

The stripe electrode 11 is an electrode divided into a plurality of electrode regions in one direction which are insulated one another. Each of the electrode regions is line-shaped. The stripe electrode 12 is equivalent to the stripe electrode 11. A size of the stripe electrode is adjustable to the size of a device for transfer. For example, it is possible to adjust wires 50 μm to 200 μm in thickness, 50 μm to 200 μm gap between wires, and 30 to 300 mm in length. As for the material of the wire, electric conductors such as platinum, copper, and zinc are available. The stripe electrode may be made in such a manner that a metal is deposited on a surface of insulator such as a glass plate and a plurality of gloves are created by a Dicing saw or a $CO_2$ laser carving machine. A voltage is applied to the stripe electrodes 11 and 12 via a conductive path 13.

Figure 26:
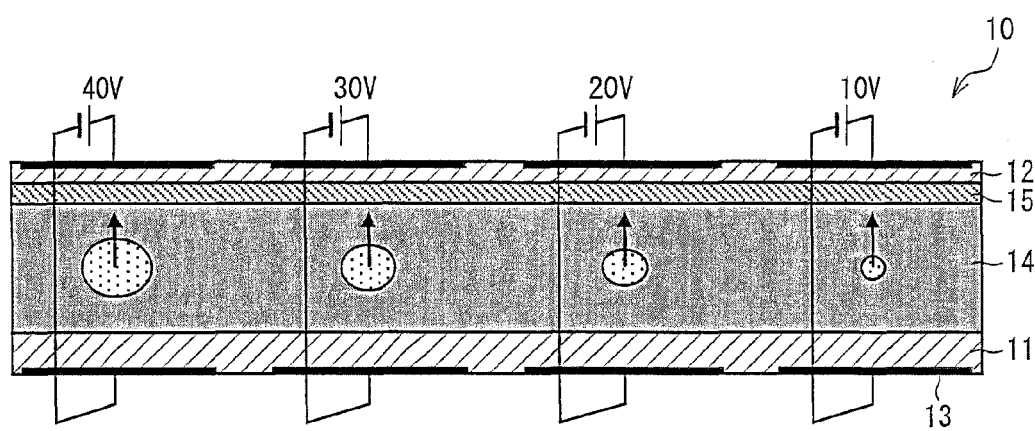
FIG. 26 is a schematic view illustrating an operation of the device for transfer according to an embodiment.

FIG. 26 is a schematic view explaining an operation of a device for transfer 10. In the device for transfer 10, in the region that high molecular weight transfer target components exist (left side in the figure), the stripe electrodes 11 and 12 are conductively connected to a high voltage power supply via the conductive path 13; in the region that low molecular weight transfer target components exist (right side in the figure), the stripe electrodes 11 and 12 are connected to a low voltage power supply via the conductive path 13. This makes it possible to apply a suitable voltage to each of the transfer target components in the first medium 14. This allows that the transfer target components are transferred from the first medium 14 to the second medium 15 efficiently. It is possible to adjust a voltage depending on the molecular weight of the transfer target components, e.g. from 1V to 500V. It is more preferable to increase the voltage from 5 to 40V stepwise or gradually from the region having low molecular weight transfer target components to the region having high molecular weight transfer target components. Also, a skillful person in the art easy to understand the most suitable applied voltage with reference to the following examples.

The following explanation deals with further another embodiment. First of all, a device for transfer 20 of the present embodiment is similar to the device for transfer 10 in FIG. 25. The device for transfer 20 includes stripe electrodes 21 and 22 (voltage applying means), and a conductive path 23 and is capable of having a first medium 24 and a second medium 25. A shape and a function of the conductive path 23, however, are different from a shape and a function of the conductive path 13. Also, the conductive path 12 is made of a resistance element.

Figure 27:
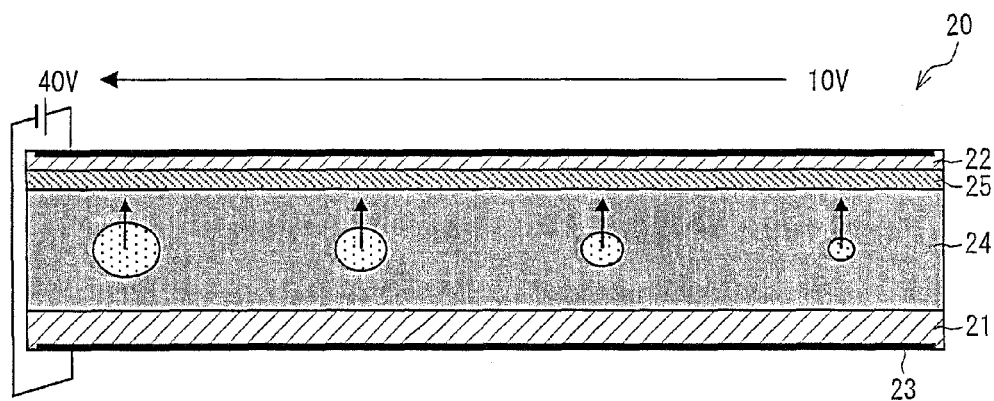
FIG. 27 is a schematic view illustrating an operation of a device for transfer according to another embodiment.

FIG. 27 is a schematic view explaining an operation of the device for transfer 20 of the present embodiment.

As illustrated in FIG. 27, the stripe electrodes 21 and 22 are conductively connected to a power supply via the conductive path 23 which is a continuous resistance element. The conductive path 23 which is conductively connected to the power supply is connected to an edge part on the side of the high molecular weight target components existing in the first medium 24. Therefore, a potential gradient is created in such a manner that the potential gradient decreases from the edge toward an opposite edge on the side of the low molecular weight target components existing in the first medium 24. This allows transferring the transfer target components efficiently from the first medium 24 to the second medium 25 by applying a suitable voltage to each of the target components. A voltage range to be used is same as the voltage range used in the device for transfer 10. A resistance value of the conductive path 23 is adjustable depending on the applied voltage, for example a resistive element whose resistance value 10Ω to 10 Ω/cm per unit length may be used.

The following explanation deals with still further another embodiment. An outline of a device for transfer 30 of the present embodiment is similar to the device for transfer 10 in FIG. 25. The device for transfer 30 includes stripe electrodes 31 and 32 (voltage applying means) and a conductive path 33, and is capable of having a first medium 34 and a second medium 35. A shape and a function of the conductive path 34, however, are different from those of the conductive path 13. Also, the conductive path 33 is a mobile and stick-shaped member.

Figure 28:
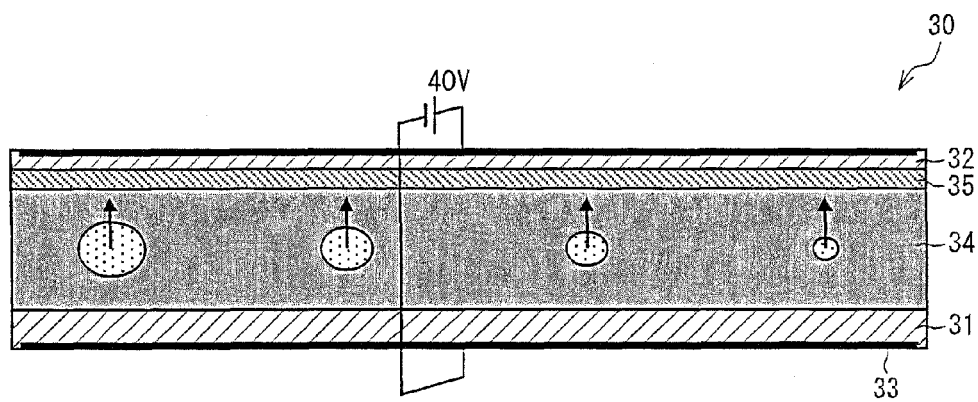
FIG. 28 is a schematic view illustrating an operation of a device for transfer according to further another embodiment.
Figure 29:
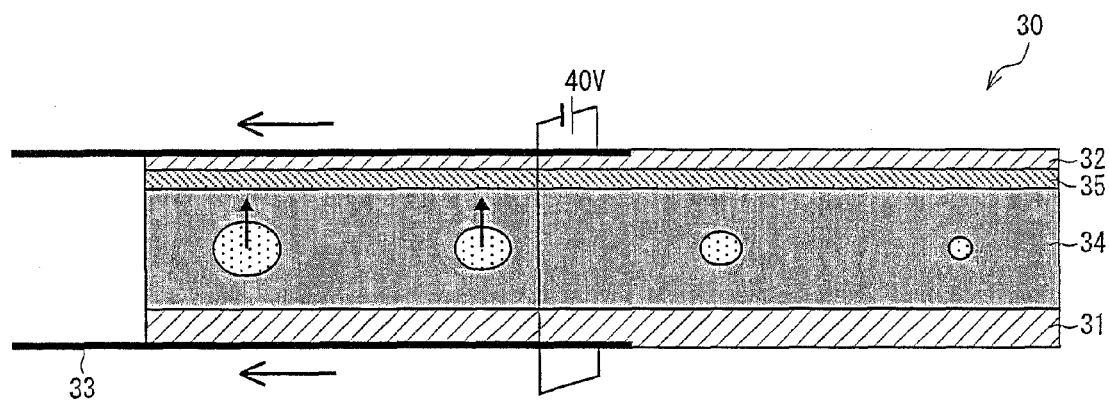
FIG. 29 is a schematic view illustrating another operation of the device for transfer according to an embodiment.

FIG. 28 is a schematic view explaining an operation of the device for transfer 30 of the present embodiment. In the device for transfer 30, the stripe electrodes 31 and 32 are applied a voltage in contact with the mobile conductive pass 33. By sliding the conductive path 33, the stripe electrodes 31 and 32 located opposite side of the sliding direction are disconnected to the conductive path 33 from the edge sequentially and a voltage is not applied to the region sandwiched between the electrodes 31 and 32 in the first medium 34 because no potential is applied between the electrodes 31 and 32. This allows applying a suitable voltage to each of the transfer target components for a suitable duration, thereby achieving efficient transfer of the transfer target components from the first medium 24 to the second medium 25. FIG. 29 is a schematic view illustrating an intermediate step of the slide. As illustrated in FIG. 29, when the conductive path 33 slides to somewhere between the ends of the electrodes 31 and 32, a potential is not applied on the stripe electrodes 11 and 12 located in the region, which has low molecular weight transfer target components (right side of the figure), so that no voltage is applied on the region any more. Namely, it is possible to apply a voltage for a suitable duration in accordance with the molecular weight of the transfer target components. As explained above, each of the transfer target components has a suitable voltage for transfer and the mobility of the transfer target component is in proportion with the product of an applied voltage and a voltage duration. Therefore, it is possible to optimize the mobility of the target component by adjusting a time period for the voltage application. The time period for the voltage application is set in consideration of an applied voltage, a transfer target component, and a composition and thickness of gel. The time period for the voltage application should be increased from 1 minute to 3 hours, or more preferably from 5 minutes to 60 minutes, from a region having low molecular weight transfer target components to a region having high molecular weight transfer target components.

Figure 30:
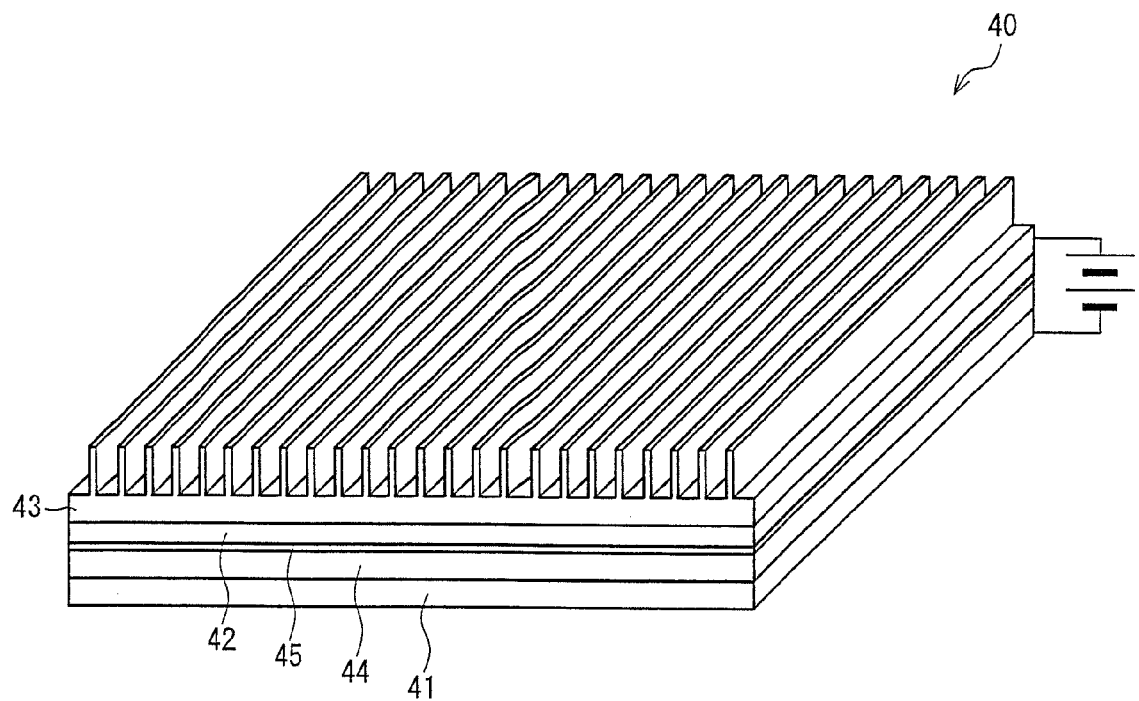
FIG. 30 is a perspective view illustrating an overall of a device for transfer according to still further another embodiment.

FIG. 30 is a perspective view illustrating an overall of a device for transfer 40. As illustrated in FIG. 30, the device for transfer 40 includes electrodes 41 and 43 (voltage applying means) and an electric resistance layer 42, and is capable of having a first medium 44 and a second medium 45.

The electric resistance layer 42 is a layer including a resistivity distribution. The resistance value of the electric resistance layer 42 varies depending on regions which are defined by an upper and a lower layers, the electrode 43 and the first medium 44, respectively. Specifically, in the electric resistance layer 42, the resistance value is set to be low over the region which has relatively high molecular weight transfer target components in the first medium 44, and is set to be high over the region which has relatively low molecular weight transfer target components in the first medium 44. Accordingly, in the medium 44, a high voltage is applied to the region which has relatively high molecular weight target components to be transferred, and a low voltage is applied to the region which has relatively low molecular weight components to be transferred. Namely, a suitable voltage to each of the transfer target components can be applied. A resistance value in the electric resistance layer 42 is not limited, but it should be ranging from several thousands Ω to ten thousands Ω.

There are various methods to form a resistivity distribution in the electric resistance layer 42. It is possible to adopt the following methods, such as distributing a plurality of materials, each of which has a different resistance value in the electric resistance layer 42, or distributing a plurality of resistive materials, each of which has a different thickness in the electric resistance layer 42. As specific examples, resin materials containing carbon materials and a known composition which is used as a resistor in general electronic components.

Figure 31:
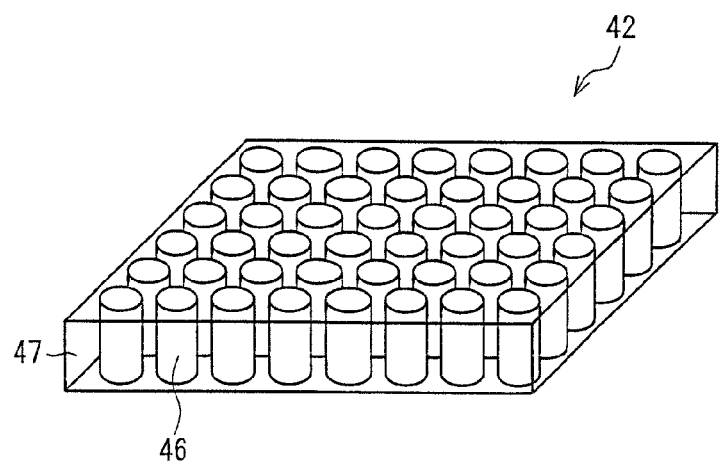
FIG. 31 is a perspective view illustrating an overall of an electric resistance sheet according to an embodiment.

FIG. 31 is a perspective view illustrating an overall of the electric resistance layer 42. As illustrated in FIG. 31, a plurality of cylindrical resistive elements 46 coupled by an insulating or high-resistance binding agent 47 are arranged in the electric resistance layer 42 in an embodiment. Namely, the resistance value has an aeolotropy in a thickness direction and in a surface direction in the present embodiment. Specifically, the electric resistance layer 42 in a thickness direction has a high resistance value defined by the cylindrical resistive element 46, and has a low resistance value defined by the binding agent 47 in a surface direction.

The cylindrical resistive element 46 has a cylindrical shape 10 μm to a few mm in diameter, or may have another shape which has a substantially equal cross sectional area, and the height is calculated in considering the resistivity value of the material of the cylindrical resistive element 46 and a resistivity distribution that the electric resistance layer 42 should have. As explained above, depending on a placement region in the electric resistance layer 42, a variety of the cylindrical resistive element 46 may be used, which has a different resistance material, a different cross sectional area, or a different density of distribution.

Figure 32:
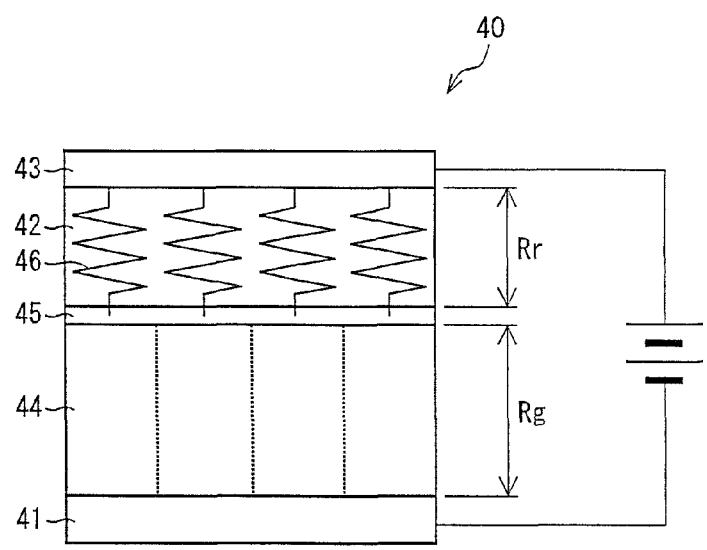
FIG. 32 is a schematic view illustrating a structure of the device for transfer according to an embodiment.

FIG. 32 is a schematic view explaining a structure of a device for transfer 40. In FIG. 32, the electric resistance layer 42 and the first medium 44 are illustrated separately into a plurality of miniregions as a concept. The following explanation is based on an assumption that currency only flows inside each of the miniregions and not to flow across a plurality of miniregions.

When applying voltage for transfer, an approximate voltage applied to each of the regions in the first medium 44 is calculated by subtracting an amount of voltage depression in the electric resistance layer 42 from the applied voltage to electrodes 41 and 43. The amount of voltage depression is calculated by a currency passing through each of the regions in the electric resistance layer 42 multiplied by a resistance value of each of the regions (Rr). If the resistance value is large, the amount of voltage depression in the region increases, thereby resulting in that the applied voltage to the first medium 44 decreases effectively. Similarly, if the resistance value is small, the amount of voltage depression in the region decreases, thereby resulting in that the applied voltage to the first medium 44 increases effectively.

Namely, it is possible to achieve an optimal transfer condition in each of the regions in the first medium 44 in such a manner that (i) a low electrical field is applied to the small molecular weight region by increasing the resistance value of the electric resistance layer 42; and (ii) a high electrical filed is applied to the large molecular weight region by decreasing the resistance value of the electric resistance layer 42.

Nonuniformity might exist in transfer target components distribution, ion distribution, and pH distribution in the first medium 44; in material distribution of the first medium 44; and in different contact state between layers such as the second medium 45 and electrodes. Because of these nonuniformities, regional resistivity variation exists in each of the miniregions in the first medium 44. In a conventional method, when a same voltage is applied to the first medium 44 entirely for transfer, an overcurrent surges to a region which has an extremely small resistance value (Rg) on the surface of the first medium 44. Therefore, there is a possibility that a fine transfer in the entire first medium 44 may not be performed.

On the other hand, the device for transfer 40 of the present embodiment, overcurrent surging to a local region is prevented by the electric resistance layer 42. This allows a fine transfer in the entire surface of gel. Namely, when an amount of current sharply increases in a local region, voltage depression in a corresponding region in electric resistance layer 42 increases. Accordingly, the voltage applied to the first medium 44 will be small. This prevents overcurrent.

Further, when polyacrylamide gel or the like is used as the first medium, a sum total of Rg of the entire first medium 44 is 50 to 500Ω. In this case, when a sum total of Rr is several thousands Ω to tens of thousands Ω, a currency passing though each region mostly depends on Rr. Therefore, the overcurrency due to nonuniformity in resistance distribution in the first medium 44, is suppressed.

As described above, the transfer device 40 including the electric resistance layer 42 of the present embodiment is capable of setting an optimal transfer condition depending on each of the regions defined by a different molecular weight of the transfer target components expanding distributed in the first medium 44, and is also capable of controlling deviation from the optimal transfer condition by preventing overcurrent surging in a local region. This allows improving transfer efficiency.

Also, the device for transfer 40 may further include cooling means for cooling the electrodes 41 and 43. This allows the first medium 44 and the second medium 45 to release heat and to maintain an optimum temperature, thereby avoiding affecting the medium or the transfer target components qualitatively.

As the cooling means, cooling components such as a radiating fin, a heat pipe, a Peltier element, a water-cooled block, and a one using a water pollination; radiation methods such as an air-cooling fan, and those combination may be used.

FIG. 30 illustrates a device for transfer 40 including a radiating fin as the cooling means. FIG. 6 illustrates a structure including a radiating fin, an anode electrode, an electric resistance layer 42, a second medium 45, a first medium 44, and a cathode electrode from the top. In addition, another structure, for example, may include a radiating fin, (radiation side) a Peltier element (cooling side), an anode electrode, an electric resistance layer 42, a second medium 45, a first medium 44, a cathode electrode; a radiating fin, (radiation side) a Peltier element (cooling side), a cathode electrode, an electric resistance layer 42, a first medium 44, a second medium 45, an electrode; or a radiating fin, an cathode electrode, an electric resistance layer 42, a first medium 44, a second medium 45, an anode electrode. The radiation method or the cooling means may be provided in either upper or lower side of the first medium 44, or in both sides.

In FIG. 30, the first medium 44 is placed in a horizontal position, however, it may be placed in a vertical position for the purpose of making a cooling efficiency uniform on both back and front sides. Also, the electric resistance layer 42 may be provided on one side in the first medium 44 or on both sides in the first medium 44. The cooling means such as a radiating fin and an electrode, both of which are provided adjacent to each other may be made of the same metal body as a joint part.

The radiating means and the cooling means are provided for maintaining an optimal temperature in the first medium 44 and the first medium 45 in such a manner that the radiating means and the cooling means radiate heat produced by the electricity flowing through the electric resistance layer 42, the first medium 44, and the first medium 45.

The radiating means and cooling means may not be used when a temperature increase in the first medium 45 is within an allowance range because a currency amount in transfer operation is small or other reasons.

Note that the electric resistance layer 42 may have a single piece construction with the electrodes 41 and 43, or may be provided as an independent member as an electric resistance sheet.

The cooling means is easy to be implemented in a device for transfer of an embodiment.

Figure 33:
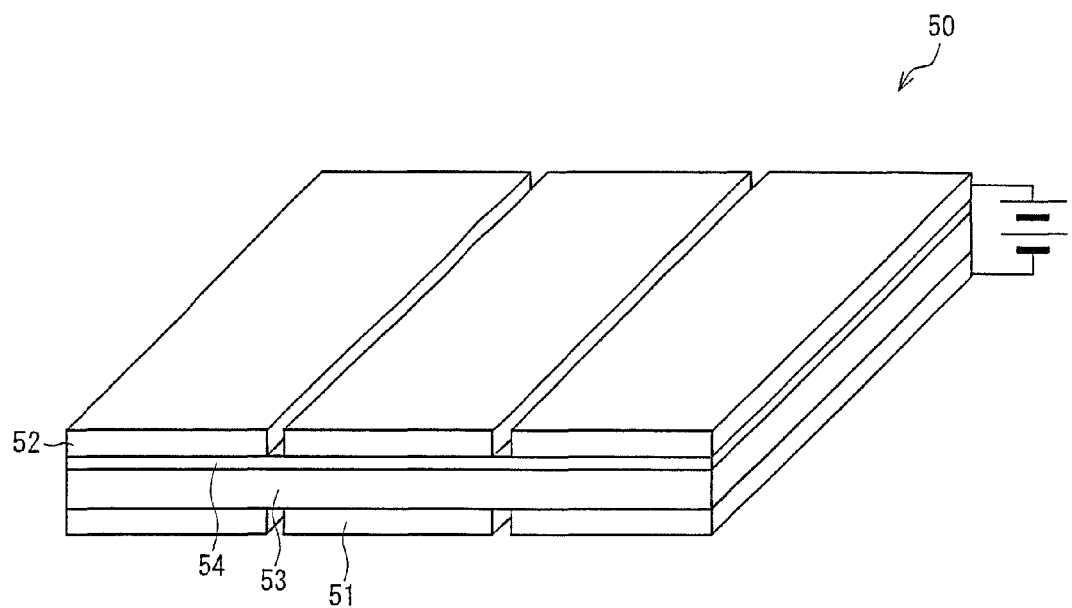
FIG. 33 is a perspective view illustrating an overall of a device for transfer according to yet another embodiment.

FIG. 33 is a perspective view illustrating an overall of the device for transfer 50 according to yet another embodiment of the present invention. As illustrated in FIG. 33, the device for transfer 50 of the present embodiment includes a plate electrodes 51 and 52 (voltage applying means) and is capable of having a first medium 53 and a second medium 54.

As illustrated in FIG. 33, the plate electrode 51 includes a plurality of electrode regions. Each of the electric region is applied a potential and applies a voltage to the first medium 53 and the second medium 54 by sandwiching between upper and lower electrode regions. A potential difference is controlled to become large when the electric regions sandwich the region which has relatively high molecular weight transfer target components in the first medium 53, and to become small when the electric regions sandwich the region which has relatively low molecular weight transfer target components in the first medium 53. It is possible to use a known technique to apply a certain potential to a certain electrode region in the plate electrodes 51 and 52. This allows an optimal voltage to be applied to each of the transfer target components.

Reference Example 2

Study of Transfer Efficiency of Protein

A protein including a variety of molecular weights was transferred by applying three different voltages 10V, 20V, and 40V and each of the transfer amounts was compared. After an SDS-PAGE with use of a commercial SDS-PAGE gel (ATTO Co.) in which SeeBlue M. W. and Dylight M. W. were applied 5 μl each, the protein including a variety of molecular weights was transferred by applying three different voltages 10V, 20V, and 40V with use of a commercial device for transfer under a standard method.

Figure 34:
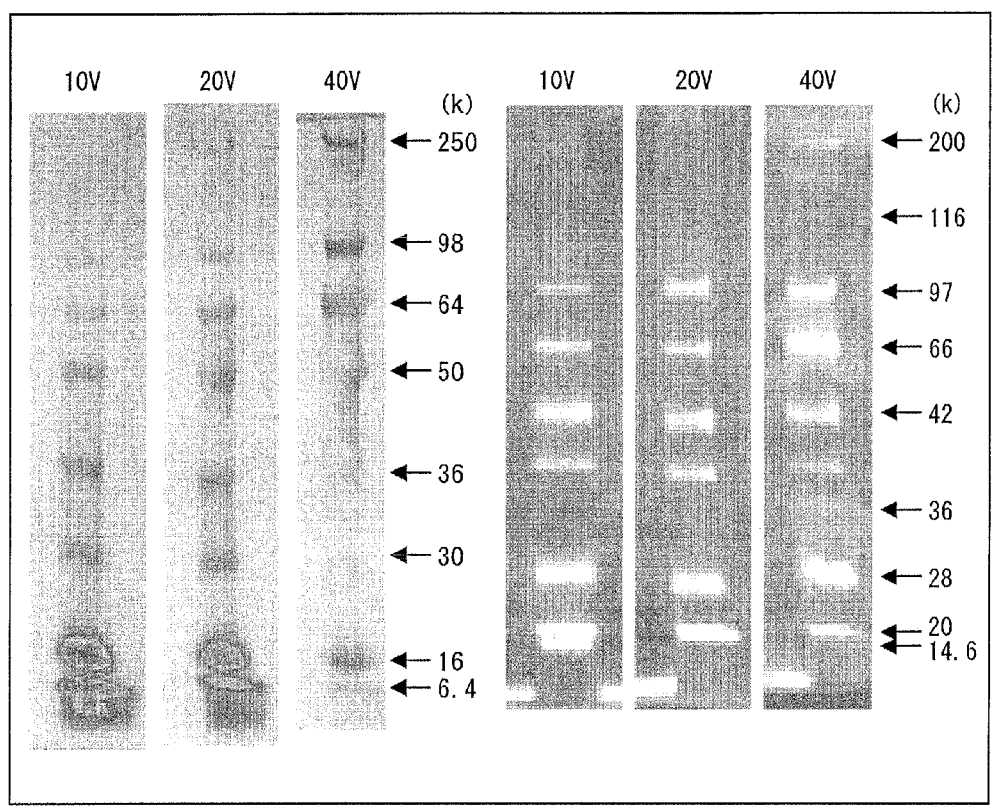
FIG. 34 is a photograph showing a result of a transfer performed by a conventional device for transfer.

A transfer buffer: 0.1% SDS, 25 mM Tris, 192 mM Glysine, and 20% Methanol was used. As a result, intensity of 200 k-64 k protein bands increased gradually as the applied voltage increased up to at 40V. On the other hand, in 50 k or less protein bands, the less molecular weight proteins reduce their intensity of protein bands and transfer amount after the applied voltage reached 20V. Note that a few k proteins were not able to be detected when it was transferred at 40V (FIG. 34).

The transfer buffer including 0.1% SDS has high transfer efficiency of high molecular weight proteins. However, it is deduced that low molecular weight proteins were not adsorbed onto the transfer membrane and allowed to pass through the transfer membrane, or diffuse on the transfer membrane. Then a similar transfer efficiency test was conducted with use of a non-SDS additive transfer buffer with the anticipation that the low molecular weight protein would not pass through the transfer membrane.

Reference Example 3

Study of a Suitable Voltage Range Depending on a Molecular Weight

Figures 35, 36:
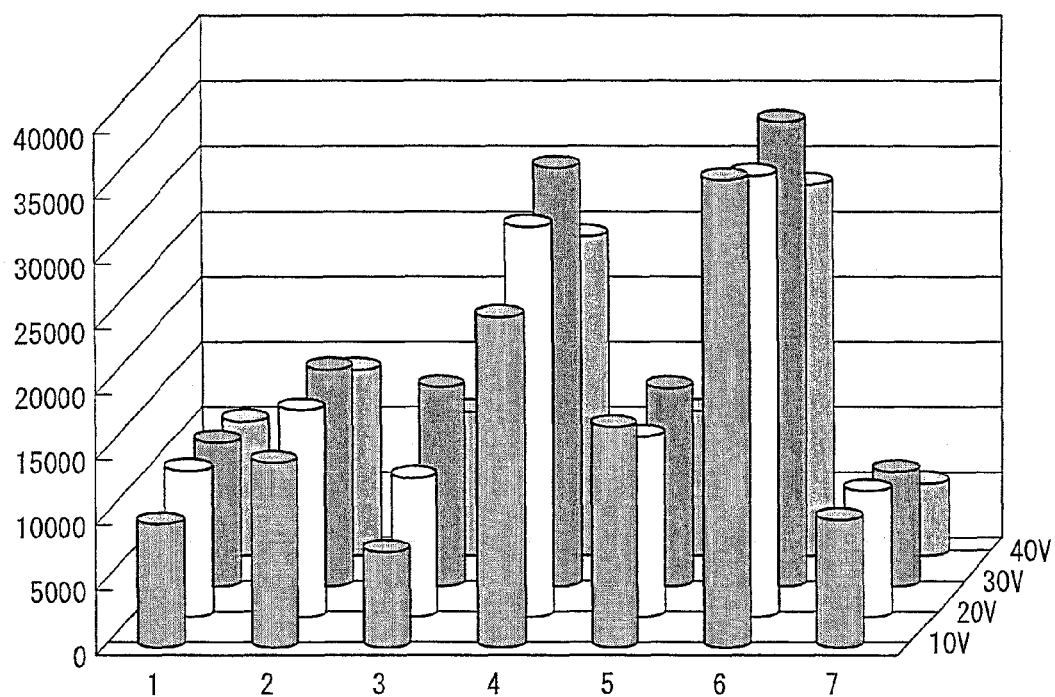
FIG. 35 is a table showing optimum transfer voltages depending molecular weights.
FIG. 36 is a graph showing optimum transfer voltages depending on molecular weights.

SeeBlue M. W. and Dylight M. W. were separated by a SDS-PAGE device (ATTO), and then were transferred with use of a non-SDS additive transfer buffer (25 mM Tris, 192 mM Glysine, and 20% Methanol) under the following voltage conditions at 10V, 20V, and 30V or 40V. Also, Dylight M.W. was transferred 4 times of each and CV (Coefficient of Variation) was calculated. As a result, the fluorescence of 200 k, 116 k, 97 k, and 66 k proteins increased as the voltage increasing from 10V to 30V. On the other hand, the fluorescence of 200 k, 116 k, 97 k, and 66 k proteins decreased as voltage increasing from 30V to 40V. Also, the fluorescence of 42 k, 36 k, and 28 k proteins peaked at 10V and decreased as the voltage increasing (FIG. 35 and FIG. 36).

According to these results, in transfer of protein, the less molecular weight protein tends to pass through a transfer membrane or diffuse on the transfer membrane. Also, this phenomenon was detected even though a PVDF membrane with high adsorbed amount of protein, 20% methanol, and non-SDS additive transfer buffer were used.

Example 9

On the basis of findings from the Reference Examples 2 and 3, the present inventors designed and produced a device for transfer which is capable of transferring transfer target components composed of different molecular weights favorably.

Figure 37:
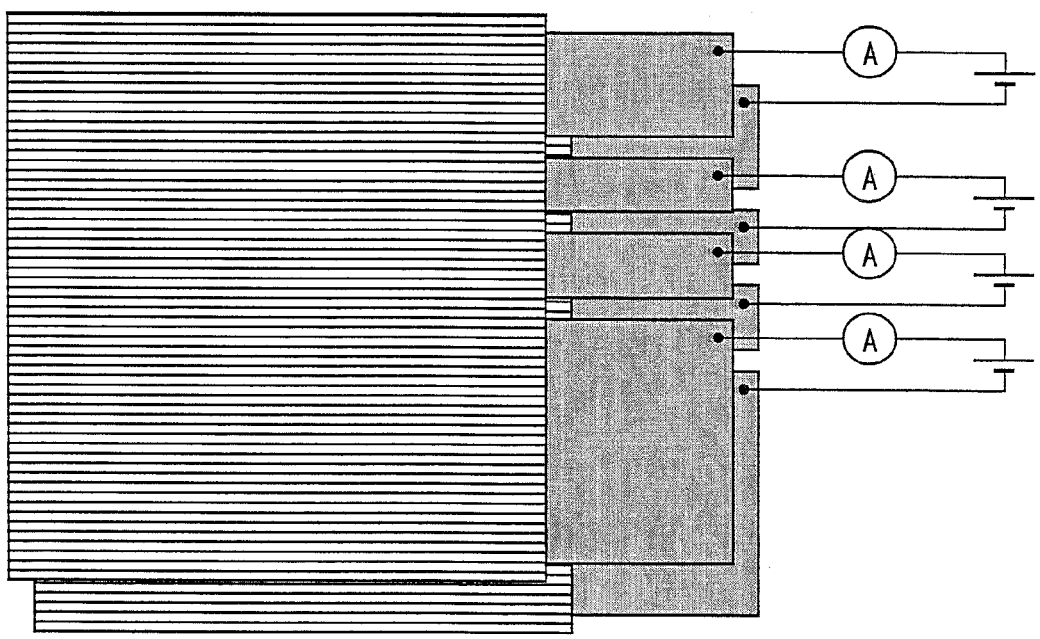
FIG. 37 is a schematic view of a device for transfer according to an embodiment.

On a blue glass plate (100 mm×82 mm), platinum lines were provided in 930 μm in width and 70 μm in space. This stripe electrode is connected to a power supply controlled by LabView via copper meshes to create an electrode which is capable of generating a potential gradient (FIG. 37).

Figure 38:
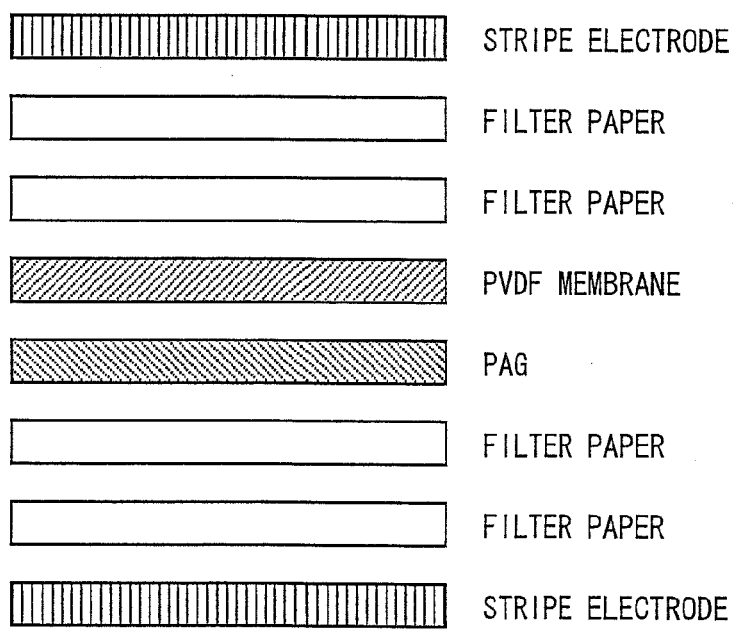
FIG. 38 is a schematic view of a device for transfer according to an embodiment.
Figure 39:
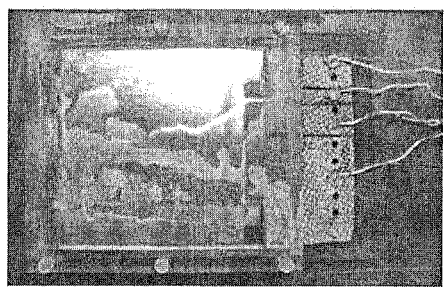
FIG. 39 is a photograph of a device for transfer according to an embodiment.

Filter papers and a PVDF membrane (Immobilon-FL, Millipore Corporation) were placed on top of the stripe electrode as illustrated in FIG. 38. FIG. 39 is the photograph.

40V, 30V, 20V, and 10V were applied in the order of high molecular weight protein. The result was illustrated in FIG. 40. In addition, 20V was applied uniformly as a control. This result is shown in FIG. 41.

Figure 40:
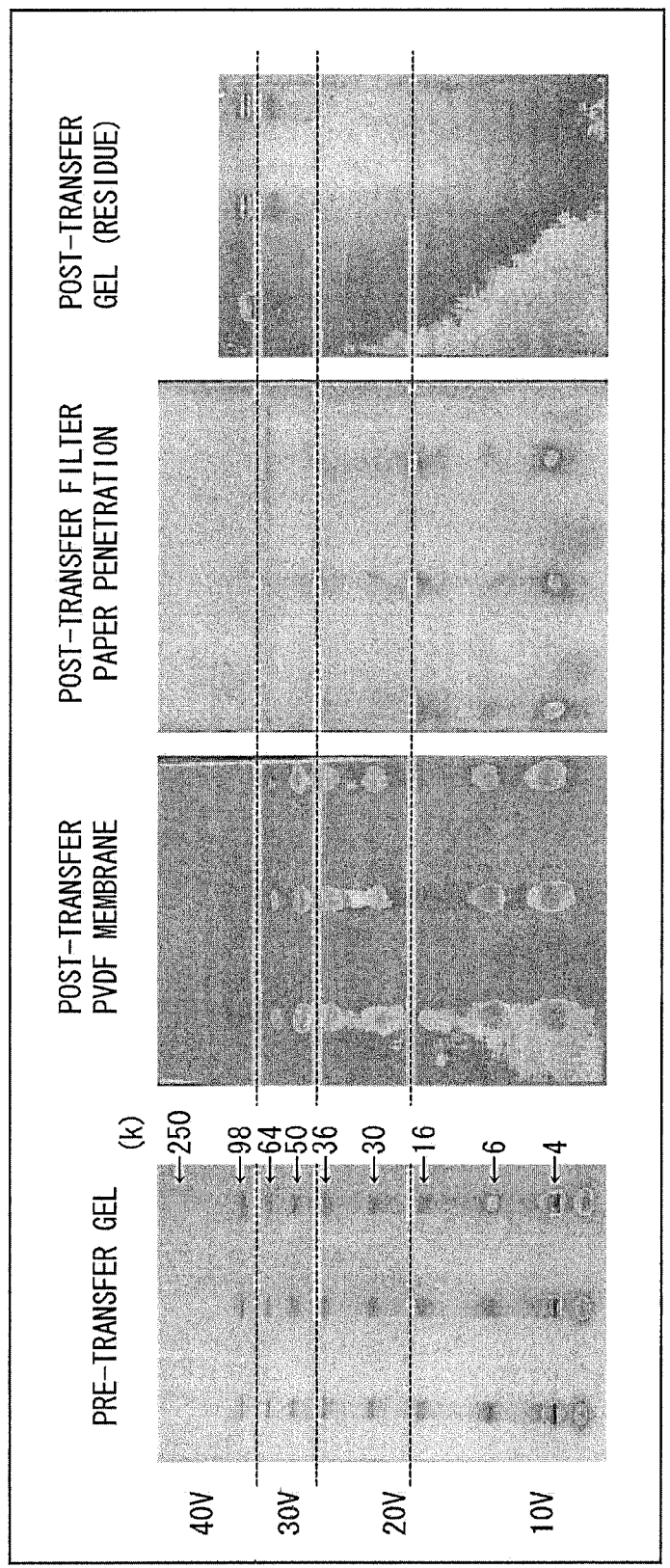
FIG. 40 is a photograph showing a result of a transfer performed by a device for transfer according to an embodiment.
Figure 41:
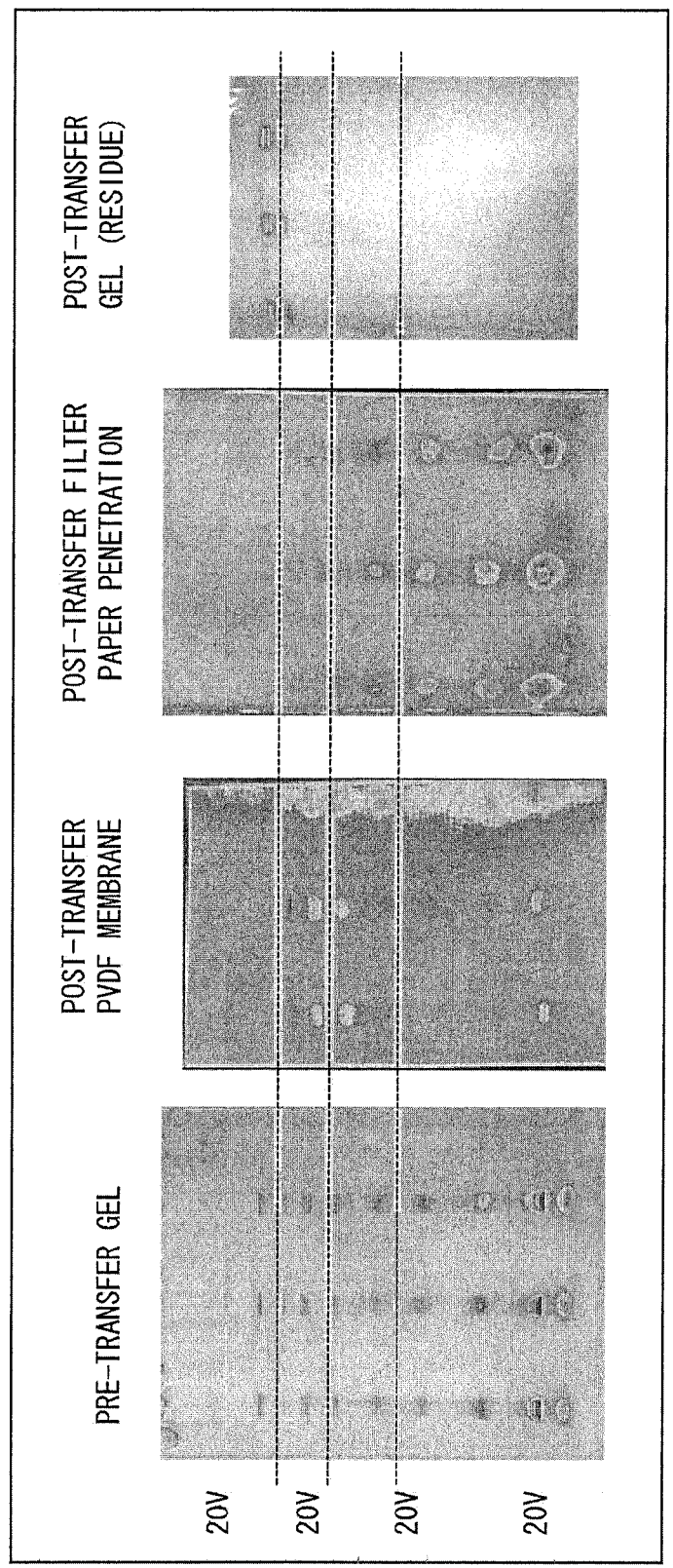
FIG. 41 is a photograph of a result of a transfer performed by a conventional device for transfer.

In comparison between FIG. 40 and FIG. 41, the device for transfer of the present invention had less proteins penetrating through a transfer membrane and more proteins were fixed in the PVDF membrane compared to a device for transfer which was applied 20V uniformly.

It is possible to provide a device for transfer preventing decline in transfer efficiency because the present embodiment can apply a suitable voltage depending on a molecular weight of a sample.

The present embodiment allows providing a device for transfer having improved transfer efficiency, which is useful for the field of analysis apparatus and the like.

The embodiments and concrete examples of implementation discussed in the foregoing detailed explanation serve solely to illustrate the technical details, which should not be narrowly interpreted within the limits of such embodiments and concrete examples, but rather may be applied in many variations within the spirit of the present embodiment, provided such variations do not exceed the scope of the patent claims set forth below.

What is claimed is:

1. A device for electrophoresis and transfer comprising:
   a separation section comprising a first medium and a second medium,
   a first buffer chamber and a second buffer chamber located on opposite ends of the separation section,
   a first electrode located in the first buffer chamber and a second electrode located in the second buffer solution chamber,
   a first stripe electrode,
   a second stripe electrode,
   wherein the first medium and the second medium are held between the first stripe electrode and the second stripe electrode so that the second medium is in contact with the first medium,
   a power supply,
   wherein the power supply is configured to apply a voltage to the first electrode and the second electrode to perform electrophoresis in the first medium,
   wherein the power supply is configured to apply a voltage to the first stripe electrode and the second stripe electrode in a direction orthogonal to an electrophoresis migration direction, and
   a mobile electric conductive section in contact with the first stripe electrode, the second stripe electrode, and the power supply, wherein
   the mobile electric conductive section is configured to slide along the first stripe electrode and second stripe electrode connecting the first stripe electrode and the second stripe electrode to the power supply wherein the duration of voltage application is altered as the mobile electric conductive section moves simultaneously along the first stripe electrode and second stripe electrode.

2. The device for electrophoresis and transfer of claim 1, wherein
   each of the first stripe electrode and the second stripe electrode is divided into a plurality of electrode regions which are insulated from one another.

3. The device for electrophoresis and transfer of claim 2, further comprising a detachable holder configured to hold the second stripe electrode and the second medium.

4. The device for electrophoresis and transfer of claim 1, further comprising a detachable holder configured to hold the second stripe electrode and the second medium.

5. A method for electrophoresis and transfer comprising;
   using the device of claim 1,
   applying a voltage to the first electrode and the second electrode in a specific direction in the first medium to separate target components in the first medium by electrophoresis,
   applying a voltage to the first medium containing the electrophoresed transfer target components using the first stripe electrode and the second stripe electrode to transfer the electrophoresed transfer target components from the first medium to the second medium wherein the voltage is applied for a suitable duration in accordance with the molecular weights of the electrophoresed transfer target components.

6. A device for transfer configured to transfer electrophoresed target components in a first medium to a second medium comprising:
   a first stripe electrode,
   a second stripe electrode,
   wherein the first medium and the second medium are held between the first stripe electrode and the second stripe electrode so that the second medium is in contact with the first medium,
   a power supply configured to apply a voltage to the first medium in a direction orthogonal to an electrophoresis migration direction of the electrophoresed transfer target components, and
   a mobile electric conductive section in contact with the first stripe electrode, the second stripe electrode, and the power supply, wherein
   the mobile electric conductive section is configured to slide along the first stripe electrode and the second stripe electrode connecting the first stripe electrode and the second stripe electrode to the power supply wherein the duration of voltage application is altered as the mobile electric conductive section moves simultaneously along the first stripe electrode and second stripe electrode.

7. The device for transfer of claim 6, wherein
   each of the first stripe electrode and the second stripe electrode is divided into a plurality of electrode regions which are insulated from one another.

8. The device for transfer of claim 6, wherein
   each of the first stripe electrode and the second stripe electrode is divided into a plurality of electrode regions which are insulated from one another and arranged in a specific direction.

9. The device for transfer of claim 7, wherein
   a shape of the plurality of electrode regions of the first stripe electrode and a shape of the plurality of regions of the second stripe electrode are substantially equal.

10. The device for transfer of claim 7, wherein
    each of the plurality of electrode regions of both the first and second stripe electrode are line-shaped.

11. The device for transfer of claim 10, wherein
    each of the plurality of the first and second stripe electrode regions are arranged in parallel to one another and extend in a direction orthogonal to the electrophoresis migration direction.

12. The device for transfer of claim 7, wherein
    the mobile electric conductive section is configured to apply a voltage to each of the plurality of first and second electrode regions.

13. The device for transfer of claim 6, wherein
    the mobile electric conductive section is bar-shaped.

14. The device for transfer of claim 6, further comprising an electric resistance layer.

15. The device for transfer of claim 6, further comprising a cooling means for cooling the first stripe electrode and the second stripe electrode.

16. A method for transferring electrophoresed transfer target components in a first medium to a second medium comprising;

using the device of claim 6, applying a voltage to the first medium containing the electrophoresed transfer target components using the first stripe electrode and the second stripe electrode to transfer the electrophoresed transfer target components from the first medium to the second medium wherein the voltage is applied for a suitable duration in accordance with the molecular weights of the electrophoresed transfer target components.

\* \* \* \* \*